United States Patent
Wood et al.

(10) Patent No.: US 7,732,128 B2
(45) Date of Patent: *Jun. 8, 2010

(54) KITS FOR DETECTION OF ATP

(75) Inventors: Keith Wood, Mt. Horeb, WI (US); Rita Hannah, Madison, WI (US); Richard A. Moravec, Oregon, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/041,323

(22) Filed: Mar. 3, 2008

(65) Prior Publication Data

US 2008/0206798 A1    Aug. 28, 2008

Related U.S. Application Data

(63) Continuation of application No. 10/895,596, filed on Jul. 21, 2004, now Pat. No. 7,452,663, which is a continuation of application No. 09/813,279, filed on Mar. 19, 2001, now Pat. No. 7,083,911.

(60) Provisional application No. 60/269,526, filed on Feb. 16, 2001.

(51) Int. Cl.
*C12Q 1/00* (2006.01)
*C07H 19/00* (2006.01)

(52) U.S. Cl. .............................. 435/4; 435/8; 536/23.2

(58) Field of Classification Search .................. None
See application file for complete search history.

(56) References Cited

U.S. PATENT DOCUMENTS

| | | | |
|---|---|---|---|
| 4,246,340 A | 1/1981 | Lundin et al. | |
| 4,303,752 A | 12/1981 | Kolehmainen et al. | |
| 4,349,510 A | 9/1982 | Kolehmainen et al. | |
| 4,906,565 A | 3/1990 | Vossen | |
| 5,004,684 A | 4/1991 | Simpson et al. | |
| 5,229,285 A | 7/1993 | Kajiyama et al. | |
| 5,258,285 A | 11/1993 | Aegidius | |
| 5,283,179 A | 2/1994 | Wood | |
| 5,558,986 A | 9/1996 | Lundin | |
| 5,618,682 A | 4/1997 | Scheirer | |
| 5,641,641 A | 6/1997 | Wood | |
| 5,648,232 A | 7/1997 | Squirrell | |
| 5,650,289 A | 7/1997 | Wood | |
| 5,814,471 A | 9/1998 | Wood | |
| 5,866,348 A | 2/1999 | Scheirer | |
| 5,891,659 A | 4/1999 | Murakami et al. | |
| 6,503,723 B1 | 1/2003 | van Lune et al. | |
| 6,660,489 B2 | 12/2003 | Schrecengost et al. | |
| 6,812,012 B1 | 11/2004 | Hattori et al. | |
| 7,083,911 B2 | 8/2006 | Wood et al. | |
| 7,422,868 B2 | 9/2008 | Fan et al. | |
| 7,452,663 B2 * | 11/2008 | Wood et al. ..................... | 435/4 |
| 2005/0048592 A1 | 3/2005 | Wood et al. | |

FOREIGN PATENT DOCUMENTS

| | | |
|---|---|---|
| EP | 1041151 A1 | 10/2000 |
| WO | WO 99/14336 | 3/1999 |
| WO | WO 99/33997 | 7/1999 |
| WO | WO 00/18953 | 4/2000 |
| WO | WO 00/49171 | 8/2000 |
| WO | WO 01/20002 | 3/2001 |

OTHER PUBLICATIONS

Andreotti, P.E. et al.; 1995; Chemosensitivity testing of human tumors using a microplate adenosine triphosphate luminescence assay, clinical correlation for cisplatin resistance of ovarian carcinoma; *Cancer Res.*; 55:5276-82.
Bradbury, D.A. et al.; 2000; Measurement of the ADP:ATP ratio in human leukaemic cell lines can be used as an indicator of cell viability, necrosis and apoptosis; *J. Immunol. Methods*; 240:79-92.
Cree, I.A.; 1998; Luminescence-based cell viability testing; *Methods Mol. Biol.*; 102:169-77.
Cree, I.A. et al.; 1997; Measurement of Cytotoxicity by ATP-based Luminescence Assay in Primary Cell Cultures and Cell Lines; *Toxicology in Vitro*; 11:553-556.
Crouch, S.P. et al; 1993; The use of ATP bioluminescence as a measure of cell proliferation and cytoxicity; *J. Immunol. Methods*; 160:81-8.
Ebadi, M.S.; 1972; Firefly luminescence in the assay of cyclic AMP; Adv. *Cyclic Nucleotide Res.*; 2:89-109.
Filippova, N.Y. et al.; 1989; New approaches to the preparation and application of firefly luciferase; *J. Biolumin. Chemilumin*; 4:419-22.
Hannah et al.; Evolution of a thermostable luciferase for application in ATP assays; International Society for Bioluminescence & Chemiluminescence; XI International Symposium 2000; General Program & Abstracts; Sep. 6-10, 2000.
Kajiyama, N. et al.; 1993; Thermostabilization of firefly luciferase by a single amino acid substitution at position 217; *Biochemistry*; 32:13795-9.
Kajiyama, N. et al.; 1994; Enhancement of thermostability of firefly luciferase from Luciola lateralis by a single amino acid substitution; *Biosci. Biotechnol. Biochem.*; 58:1170-1.
Kangas, L.M. et al.; 1984; Bioluminescence of cellular ATP: a new method for evaluating cytotoxic agents in vitro; *Med. Biol.*; 62:338-43.
Kricka, L.J. et al.; 1982; Effect of solvents on the catalytic activity of firefly luciferase; *Arch. Biochem. Biophys.*; 217:674-81.
Kuzmits, R. et al.; 1986; Assessment of the sensitivity of leukaemic cells to cytotoxic drugs by bioluminescence measurement of ATP in cultured cells; *Clinical Science*; 71, 81-88.

(Continued)

*Primary Examiner*—Anand U Desai
(74) *Attorney, Agent, or Firm*—Michael Best & Friedrich LLP

(57) ABSTRACT

Methods and kits for detecting the presence of ATP, for measuring ATP concentrations, and for detecting viable cells using a composition comprising an ATP-dependent enzyme and one or more ATPase inhibitors.

14 Claims, 2 Drawing Sheets

OTHER PUBLICATIONS

Promega Technical Manual; Dual-Luciferase Reporter 1000 Assay System; May 1999.

Ronner, P.E.; 1999; Luminometric assays of ATP, phosphocreatine, and creatine for estimation of free ADP and free AMP; *Anal. Biochem.*; 275:208-16.

Simpson, W.J. and J.R. Hammond; 1991; The effect of detergents on firefly luciferase reactions [published erratum appears in J. Biolumin Chemilumin. 1991]; July-September; 6(3):146]; *J. Biolumin Chemilumin*; 6:97-106.

Stanley, P.E.; 1989; A review of bioluminescent ATP techniques in rapid microbiology; *J. Biolumin Chemilumin*; 4:375-80.

White. P.J. et al.; 1996; Improved thermostability of the North American firefly luciferase: saturation mutagenesis at position 354; *Biochem J.*; 319:343-50.

Wood, K.V. et al.; 1989; Introduction to beetle luciferases and their applications; *J. Biolumin Chemilumin*; 4:289-301.

Groth, G. et al.; 1996; ATP synthase from bovine heart mitochondria: reconstitution into unilamellar phospholipid vesicles of the pure enzyme in a functional state; Biochem. J.; 318:351-57.

* cited by examiner

SEQUENCE LISTING

```
<160> NUMBER OF SEQ ID NOS: 8

<210> SEQ ID NO 1
<211> LENGTH: 544
<212> TYPE: PRT
<213> ORGANISM: Artificial
<220> FEATURE:
<223> OTHER INFORMATION: Mutant luciferase, LucPpe2m78 (i.e., 78-0B10)
      amino acid sequence

<400> SEQUENCE: 1

Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Asp Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125
```

-continued

```
Lys Asn Thr Phe Gln Lys Val Leu Asn Val Lys Ser Lys Leu Lys Ser
130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Phe Glu Lys His Thr Asn Gly
    530                 535                 540
```

```
<210> SEQ ID NO 2
<211> LENGTH: 544
<212> TYPE: PRT
<213> ORGANISM: Artificial
<220> FEATURE:
<223> OTHER INFORMATION: Mutant luciferase, LucPpe2m90 (i.e., 90-1B5)
      amino acid sequence

<400> SEQUENCE: 2
```

| | | | | | | | | | | | | | | |
|---|---|---|---|---|---|---|---|---|---|---|---|---|---|---|
| Met | Ala | Asp | Lys | Asn | Ile | Leu | Tyr | Gly | Pro | Glu | Pro | Phe | Tyr | Pro | Leu |
| 1 | | | | 5 | | | | | 10 | | | | | 15 | |

| Glu | Asp | Gly | Thr | Ala | Gly | Glu | Gln | Met | Phe | Asp | Ala | Leu | Ser | Arg | Tyr |
|---|---|---|---|---|---|---|---|---|---|---|---|---|---|---|---|
| | | | 20 | | | | | 25 | | | | | 30 | | |

| Ala | Asp | Ile | Pro | Gly | Cys | Ile | Ala | Leu | Thr | Asn | Ala | His | Thr | Lys | Glu |
|---|---|---|---|---|---|---|---|---|---|---|---|---|---|---|---|
| | | 35 | | | | | 40 | | | | | 45 | | | |

| Asn | Val | Leu | Tyr | Glu | Glu | Phe | Leu | Lys | Leu | Ser | Cys | Arg | Leu | Ala | Glu |
|---|---|---|---|---|---|---|---|---|---|---|---|---|---|---|---|
| | 50 | | | | | 55 | | | | | 60 | | | | |

| Ser | Phe | Lys | Lys | Tyr | Gly | Leu | Lys | Gln | Asn | Asp | Thr | Ile | Ala | Val | Cys |
|---|---|---|---|---|---|---|---|---|---|---|---|---|---|---|---|
| 65 | | | | | 70 | | | | | 75 | | | | | 80 |

| Ser | Glu | Asn | Gly | Leu | Gln | Phe | Phe | Leu | Pro | Val | Ile | Ala | Ser | Leu | Tyr |
|---|---|---|---|---|---|---|---|---|---|---|---|---|---|---|---|
| | | | | 85 | | | | | 90 | | | | | 95 | |

| Leu | Gly | Ile | Ile | Val | Ala | Pro | Val | Asn | Asp | Lys | Tyr | Ile | Glu | Arg | Glu |
|---|---|---|---|---|---|---|---|---|---|---|---|---|---|---|---|
| | | | 100 | | | | | 105 | | | | | 110 | | |

| Leu | Ile | His | Ser | Leu | Gly | Ile | Val | Lys | Pro | Arg | Ile | Val | Phe | Cys | Ser |
|---|---|---|---|---|---|---|---|---|---|---|---|---|---|---|---|
| | | 115 | | | | | 120 | | | | | 125 | | | |

| Lys | Asn | Thr | Phe | Gln | Lys | Val | Leu | Asn | Val | Lys | Ser | Lys | Leu | Lys | Ser |
|---|---|---|---|---|---|---|---|---|---|---|---|---|---|---|---|
| | 130 | | | | | 135 | | | | | 140 | | | | |

| Ile | Glu | Thr | Ile | Ile | Ile | Leu | Asp | Leu | Asn | Glu | Asp | Leu | Gly | Gly | Tyr |
|---|---|---|---|---|---|---|---|---|---|---|---|---|---|---|---|
| 145 | | | | | 150 | | | | | 155 | | | | | 160 |

| Gln | Cys | Leu | Asn | Asn | Phe | Ile | Ser | Gln | Asn | Ser | Asp | Ser | Asn | Leu | Asp |
|---|---|---|---|---|---|---|---|---|---|---|---|---|---|---|---|
| | | | | 165 | | | | | 170 | | | | | 175 | |

| Val | Lys | Lys | Phe | Lys | Pro | Tyr | Ser | Phe | Asn | Arg | Asp | Asp | Gln | Val | Ala |
|---|---|---|---|---|---|---|---|---|---|---|---|---|---|---|---|
| | | | 180 | | | | | 185 | | | | | 190 | | |

| Leu | Ile | Met | Phe | Ser | Ser | Gly | Thr | Thr | Gly | Leu | Pro | Lys | Gly | Val | Met |
|---|---|---|---|---|---|---|---|---|---|---|---|---|---|---|---|
| | | 195 | | | | | 200 | | | | | 205 | | | |

| Leu | Thr | His | Lys | Asn | Ile | Val | Ala | Arg | Phe | Ser | Leu | Ala | Lys | Asp | Pro |
|---|---|---|---|---|---|---|---|---|---|---|---|---|---|---|---|
| | 210 | | | | | 215 | | | | | 220 | | | | |

| Thr | Phe | Gly | Asn | Ala | Ile | Asn | Pro | Thr | Thr | Ala | Ile | Leu | Thr | Val | Ile |
|---|---|---|---|---|---|---|---|---|---|---|---|---|---|---|---|
| 225 | | | | | 230 | | | | | 235 | | | | | 240 |

| Pro | Phe | His | His | Gly | Phe | Gly | Met | Met | Thr | Thr | Leu | Gly | Tyr | Phe | Thr |
|---|---|---|---|---|---|---|---|---|---|---|---|---|---|---|---|
| | | | | 245 | | | | | 250 | | | | | 255 | |

| Cys | Gly | Phe | Arg | Val | Val | Leu | Met | His | Thr | Phe | Glu | Glu | Lys | Leu | Phe |
|---|---|---|---|---|---|---|---|---|---|---|---|---|---|---|---|
| | | | 260 | | | | | 265 | | | | | 270 | | |

| Leu | Gln | Ser | Leu | Gln | Asp | Tyr | Lys | Val | Glu | Ser | Thr | Leu | Leu | Val | Pro |
|---|---|---|---|---|---|---|---|---|---|---|---|---|---|---|---|
| | | 275 | | | | | 280 | | | | | 285 | | | |

| Thr | Leu | Met | Ala | Phe | Leu | Ala | Lys | Ser | Ala | Leu | Val | Glu | Lys | Tyr | Asp |
|---|---|---|---|---|---|---|---|---|---|---|---|---|---|---|---|
| | 290 | | | | | 295 | | | | | 300 | | | | |

| Leu | Ser | His | Leu | Lys | Glu | Ile | Ala | Ser | Gly | Gly | Ala | Pro | Leu | Ser | Lys |
|---|---|---|---|---|---|---|---|---|---|---|---|---|---|---|---|
| 305 | | | | | 310 | | | | | 315 | | | | | 320 |

| Glu | Ile | Gly | Glu | Met | Val | Lys | Lys | Arg | Phe | Lys | Leu | Asn | Phe | Val | Arg |
|---|---|---|---|---|---|---|---|---|---|---|---|---|---|---|---|
| | | | | 325 | | | | | 330 | | | | | 335 | |

| Gln | Gly | Tyr | Gly | Leu | Thr | Glu | Thr | Thr | Ser | Ala | Val | Leu | Ile | Thr | Pro |
|---|---|---|---|---|---|---|---|---|---|---|---|---|---|---|---|
| | | | 340 | | | | | 345 | | | | | 350 | | |

| Lys | Gly | Asp | Ala | Lys | Pro | Gly | Ser | Thr | Gly | Lys | Ile | Val | Pro | Phe | His |
|---|---|---|---|---|---|---|---|---|---|---|---|---|---|---|---|
| | | 355 | | | | | 360 | | | | | 365 | | | |

```
Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
                500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Thr Asn Gly
        530                 535                 540

<210> SEQ ID NO 3
<211> LENGTH: 544
<212> TYPE: PRT
<213> ORGANISM: Artificial
<220> FEATURE:
<223> OTHER INFORMATION: Mutant luciferase, LucPpe2m133 (i.e., 133-1B2)
      amino acid sequence

<400> SEQUENCE: 3

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Asp Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Asp Asp Leu Gly Gly Tyr
145                 150                 155                 160

Gln Cys Leu Asn Asn Phe Ile Ser Gln Asn Ser Asp Ser Asn Leu Asp
                165                 170                 175
```

```
Val Lys Lys Phe Lys Pro Tyr Ser Phe Asn Arg Asp Asp Gln Val Ala
            180                 185                 190

Leu Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
            210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Lys Gly Asp Ala Lys Pro Gly Ser Thr Gly Lys Ile Val Pro Phe His
                355                 360                 365

Ala Val Lys Val Val Asp Pro Thr Thr Gly Lys Ile Leu Gly Pro Asn
            370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Ile Phe Leu Asp Glu Ile Pro Lys Gly Ser Thr Gly Lys
            515                 520                 525

Ile Asp Arg Lys Val Leu Arg Gln Met Leu Glu Lys His Thr Asn Gly
            530                 535                 540

<210> SEQ ID NO 4
<211> LENGTH: 544
<212> TYPE: PRT
<213> ORGANISM: Artificial
<220> FEATURE:
<223> OTHER INFORMATION: Mutant luciferase, LucPpe2m146 (i.e., 146-1H2)
      amino acid sequence
```

<400> SEQUENCE: 4

```
Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
            85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
    210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Leu His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415
```

```
Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
        450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Leu Glu Lys His Thr Asn Gly
    530                 535                 540

<210> SEQ ID NO 5
<211> LENGTH: 1639
<212> TYPE: DNA
<213> ORGANISM: Artificial
<220> FEATURE:
<223> OTHER INFORMATION: 78-0B10 nucleic acid sequence

<400> SEQUENCE: 5
ggatccaatg gcagataaga atattttata tgggcccgaa ccatttttatc ccttggctga      60 tgggacggct ggagaacaga tgtttgacgc attatctcgt tatgcagata tttccggatg     120
catagcattg acaaatgctc atacaaaaga aaatgtttta tatgaagagt ttttaaaatt     180
gtcgtgtcgt ttagcggaaa gttttaaaaa gtatggatta aaacaaaacg acacaatagc     240
ggtgtgtagc gaaaatggtt tgcaattttt ccttcctgta attgcatcat tgtatcttgg     300
aataattgca gcacctgtta gtgataaata cattgaacgt gaattaatac acagtcttgg     360
tattgtaaaa ccacgcataa ttttttgctc aagaatact tttcaaaaag tactgaatgt      420
aaaatctaaa ttaaaatctg tagaaactat tattatatta gacttaaatg aagcttaggg     480
aggttatcaa tgcctcaaca actttatttc tcaaaattcc gatagtaatc tggacgtaaa     540
aaaatttaaa ccatattctt ttaatcgaga cgatcaggtt gcgttggtaa tgttttcttc      600
tggtacaact ggtgttccga agggagtcat gctaactcac aagaatattg ttgcacgatt     660
ttctcttgca aagatccta cttttggtaa cgcaattaat cccacgacag caattttaac      720
ggtaatacct ttccaccatg gttttggtat gatgaccaca ttaggatact ttacttgtgg     780
attccgagtt gttctaatgc acacgtttga agaaaaacta tttctacaat cattacaaga     840
ttataaagtg gaaagtactt tacttgtacc aacattaatg gcatttcttg caaaaagtgc     900
attagttgaa aagtacgatt tatcgcactt aaaagaaatt gcatctggtg gcgcaccttt     960
atcaaaagaa attggggaga tggtgaaaaa acggtttaaa ttaaactttg tcaggcaagg    1020
gtatggatta acagaaacca cttcggctgt tttaattaca ccgaaaggtg acgccagacc    1080
gggatcaact ggtaaaatag taccatttca cgctgttaaa gttgtcgatc ctacaacagg    1140
aaaaattttg gggccaaatg aacctggaga attgtatttt aaaggcgcca tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
```

```
gtcattaatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattttgtt tccagtcaag tttcaacagc caaatggcta cgtggtgggg tgaaattttt    1560
ggatgaaatt cccaaaggat caactggaaa aattgacaga aaagtgttaa gacaaatgtt    1620
tgaaaaacac accaatggg                                                 1639
```

<210> SEQ ID NO 6  
<211> LENGTH: 1639  
<212> TYPE: DNA  
<213> ORGANISM: Artificial  
<220> FEATURE:  
<223> OTHER INFORMATION: 90-1B5 nucleic acid sequence

<400> SEQUENCE: 6

```
ggatccaatg gcagataaga atattttata tgggcccgaa ccatttatc ccttggaaga     60 tgggacggct ggagaacaga tgtttgacgc attatctcgt tatgcagata ttccgggctg    120
catagcattg acaaatgctc atacaaaaga aaatgtttta tatgaagagt ttctgaaact    180
gtcgtgtcgt ttagcggaaa gttttaaaaa gtatggatta aaacaaaacg acacaatagc    240
ggtgtgtagc gaaaatggtc tgcaattttt ccttcctgta attgcatcat tgtatcttgg    300
aataattgtg gcacctgtta acgataaata cattgaacgt gaattaatac acagtcttgg    360
tattgtaaaa ccacgcatag tttttgctc aagaatact tttcaaaaag tactgaatgt     420
aaaatctaaa ttaaaatcta ttgaaactat tattatatta gacttaaatg aagacttagg    480
aggttatcaa tgcctcaaca actttatttc tcaaaattcc gatagtaatc tggacgtaaa    540
aaaatttaaa ccatattctt ttaatcgaga cgatcaggtt gcgttgatta tgttttcttc    600
tggtacaact ggtctgccga agggagtcat gctaactcac aagaatattg ttgcacgatt    660
ttctcttgca aaagatccta cttttggtaa cgcaattaat cccacgacag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcacccttt   960 atcaaaagaa attggggaga tggtgaaaaa acggtttaaa ttaaactttg tcaggcaagg   1020
gtatggatta acagaaacca cttcggctgt tttaattaca ccgaaaggtg acgccaaacc    1080
gggatcaact ggtaaaatag taccatttca cgctgttaaa gttgtcgatc ctacaacagg    1140
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattatgtt gccagtcaag tttcaacagc caaatggcta cgtggtgggg tgaaattttt    1560
ggatgaaatt cccaaaggat caactggaaa aattgacaga aaagtgttaa gacaaatgtt    1620
tgaaaaacac accaatggg                                                1639
```

<210> SEQ ID NO 7
<211> LENGTH: 1639
<212> TYPE: DNA
<213> ORGANISM: Artificial
<220> FEATURE:
<223> OTHER INFORMATION: 133-1B2 nucleic acid sequence

<400> SEQUENCE: 7

| | | | | | |
|---|---|---|---|---|---|
| agatccaatg | gcagataaga | atattttata | tgggcccgaa | ccattttatc | ccttggaaga | 60 |
| tgggacggct | ggagaacaga | tgtttgacgc | attatctcgt | tatgcagata | ttccgggctg | 120 |
| catagcattg | acaaatgctc | atacaaaaga | aaatgtttta | tatgaagagt | ttctgaaact | 180 |
| gtcgtgtcgt | ttagcggaaa | gttttaaaaa | gtatggatta | aaacaaaacg | acacaatagc | 240 |
| ggtgtgtagc | gaaaatagtc | tgcaattttt | ccttcctgta | attgcatcat | tgtatcttgg | 300 |
| aataattgtg | gcacctgtta | acgataaata | cattgaacgt | gaattaatac | acagtcttgg | 360 |
| tattgtaaaa | ccacgcatag | ttttttgctc | caagaatact | tttcaaaaag | tactgaatgt | 420 |
| aaaatctaaa | ttaaaatcta | ttgaaactat | tattatatta | gacttaaatg | atgacttagg | 480 |
| aggttatcaa | tgcctcaaca | actttatttc | tcaaaattcc | gatagtaatc | tggacgtaaa | 540 |
| aaaatttaaa | ccatattctt | ttaatcgaga | cgatcaggtt | gcgttgatta | tgttttcttc | 600 |
| tggtacaact | ggtctgccga | agggagtcat | gctaactcac | aagaatattg | ttgcacgatt | 660 |
| ttctattgca | aaagatccta | ctttttggtaa | cgcaattaat | cccacgtcag | caattttaac | 720 |
| ggtaatacct | ttccaccatg | gttttggtat | gatgaccaca | ttaggatact | ttacttgtgg | 780 |
| attccgagtt | gttctaatgc | acacgtttga | agaaaaacta | tttctacaat | cattacaaga | 840 |
| ttataaagtg | gaaagtactt | tacttgtacc | aacattaatg | gcatttcttg | caaaaagtgc | 900 |
| attagttgaa | aagtacgatt | tatcgcactt | aaaagaaatt | gcatctggtg | gcgcacccttt | 960 |
| atcaaaagaa | attggggaga | tggtgaaaaa | acggtttaaa | ttaaactttg | tcaggcaagg | 1020 |
| gtatggatta | acagaaacca | cttcggctgt | tttaattaca | ccgaaaggtg | acgccaaacc | 1080 |
| gggatcaact | ggtaaaatag | taccatttca | cgctgttaaa | gttgtcgatc | ctacaacagg | 1140 |
| aaaaattttg | gggccaaatg | aacctggaga | attgtatttt | aaaggcccga | tgataatgaa | 1200 |
| gggttattat | aataatgaag | aagctactaa | agcaattatt | gataatgacg | gatggttgcg | 1260 |
| ctctggtgat | attgcttatt | atgacaatga | tggccatttt | tatattgtgg | acaggctgaa | 1320 |
| gtcactgatt | aaatataaag | gttatcaggt | tgcacctgct | gaaattgagg | gaatactctt | 1380 |
| acaacatccg | tatattgttg | atgccggcgt | tactggtata | ccggatgaag | ccgcgggcga | 1440 |
| gcttccagct | gcaggtgttg | tagtacagac | tggaaaatat | ctaaacgaac | aaatcgtaca | 1500 |
| agattatgtt | gccagtcaag | tttcaacagc | caaatggcta | cgtggtgggg | tgatattttt | 1560 |
| ggatgaaatt | cccaaaggat | caactggaaa | aattgacaga | aaagtgttaa | gacaaatgtt | 1620 |
| agaaaaacac | accaatggg | | | | | 1639 |

<210> SEQ ID NO 8
<211> LENGTH: 1639
<212> TYPE: DNA
<213> ORGANISM: Artificial
<220> FEATURE:
<223> OTHER INFORMATION: 146-1H2 nucleic acid sequence

<400> SEQUENCE: 8

| | | | | | |
|---|---|---|---|---|---|
| ggatccaatg | gcagataaga | atattttata | tgggcccgaa | ccattttatc | ccttggaaga | 60 |
| tgggacggct | ggagaacaga | tgtttgacgc | attatctcgt | tatgcagcta | ttccgggctg | 120 |

-continued

```
catagcattg acaaatgctc atacaaaaga aaatgtttta tatgaagagt ttctgaaact    180
gtcgtgtcgt ttagcggaaa gttttaaaaa gtatggatta aaacaaaacg acacaatagc    240
ggtgtgtagc gaaaatagtc tgcaatttt  ccttcctgta attgcatcat tgtatcttgg    300
aataattgtg gcacctgtta acgataaata cattgaacgt gaattaatac acagtcttgg    360
tattgtaaaa ccacgcatag ttttttgctc caagaatact tttcaaaaag tactgaatgt    420
aaaatctaaa ttaaaatcta ttgaaactat tattatatta gacttaaatg aagacttagg    480
aggttatcaa tgcctcaaca actttatttc tcaaaattcc gatagtaatc tggacgtaaa    540
aaaatttaaa ccctattctt ttaatcgaga cgatcaggtt gcgtcgatta tgttttcttc    600
tggtacaact ggtctgccga agggagtcat gctaactcac aagaatattg ttgcacgatt    660
ttctattgca aaagatccta cttttggtaa cgcaattaat cccacgtcag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcacctt    960
atcaaaagaa attggggaga tggtgaaaaa acggtttaaa ttaaactttg tcaggcaagg   1020
gtatggatta acagaaacca cttcggctgt tttaattaca ccgaaaggtg acgccaaacc   1080
gggatcaact ggtaaaatag taccattaca cgctgttaaa gttgtcgatc ctacaacagg   1140
aaaaattttg gggccaaatg aacctggaga attgtatttt aaaggcccga tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcactgatt aaatataaag gttatcaggt tgcacctgct gaaattgagg aatactctt    1380
acaacatccg tatattgttg atgccggcgt tactggtata ccggatgaag ccgcgggcga   1440
gcttccagct gcaggtgttg tagtacagac tggaaaatat ctaaacgaac aaatcgtaca   1500
agattatgtt gccagtcaag tttcaacagc caaatggcta cgtggtgggg tgaaatttt    1560
ggatgaaatt cccaaaggat caactggaaa aattgacaga aaagtgttaa gacaaatgtt   1620
agaaaaacac accaatggg                                                1639
```

KITS FOR DETECTION OF ATP

CROSS REFERENCE TO RELATED APPLICATIONS

This application is a continuation of U.S. patent application Ser. No. 10/895,596, entitled KITS FOR DETECTION OF ATP, filed on Jul. 21, 2004, now U.S. Pat. No. 7,452,663, which is a continuation of U.S. patent application Ser. No. 09/813,279 entitled METHOD FOR MEASUREMENT OF ATP, filed on Mar. 19, 2001, now U.S. Pat. No. 7,083,911, which claims the benefit of U.S. Provisional Patent Application 60/269,526 filed on Feb. 16, 2001. All of these priority patent applications list Keith Wood, Rita Hannah, and Richard A. Moravec as inventors and are incorporated herein by reference in their entirety.

FIELD OF THE INVENTION

The present invention relates generally to the fields of cell biology and molecular biology. In particular, this invention relates to methods, compositions and kits for improving the detection and quantitation of ATP.

BACKGROUND OF THE INVENTION

Advances in the biological, biomedical and pharmaceutical sciences have accelerated the pace of research and diagnostics unparalleled in the past. With whole genome sequences becoming quickly and successively available, the assembly of large libraries of small molecules, and the ability to move pharmaceutical development, clinical diagnostic tests and basic research from a reductionist to a whole system approach demands assays that facilitate high throughput analyses. Molecules no longer need to be singly analyzed for their effects on a lone process; instead, the effects of many molecules on several biological systems can be studied simultaneously—if appropriate, fast, reliable, and accurate assays are available.

Preferred bioassays that assist in evaluating cellular health are those that detect and quantify adenosine triphosphate (ATP). Hydrolysis of ATP powers many of a cell's biochemical processes. Healthy, viable cells are rich in ATP; dead or dying cells are ATP-poor.

Efficient, reliable and accurate assays for cell viability can be used to rapidly discover cytotoxic agents or cell proliferation agents and determine the cytotoxic effect or cell proliferation effect of agents on cells. Cancer pharmaceutical research often endeavors to identify compounds that selectively kill quickly-dividing cells—a primary characteristic of cancer cells. While some effective anti-cancer cytotoxic compounds have been identified; innumerable potentially more valuable compounds await identification. High throughput screens of compound libraries, coupled with efficient cell viability assays, can swiftly identify such compounds. In some systems of the body, controlled cell death is crucial for appropriate function. For example, immune system development—a continual process—depends on apoptosis (programmed cell death). The discovery of drugs to treat immuno-related dysfunctions often depends on determining cell viability. The efficacy of a candidate compound on cell viability can be assayed by detecting ATP, since ATP production is only realized in metabolically active (live) cells and residual ATP in a cell is degraded upon cell death, particularly quickly in non-apoptotic (necrotic) cell death. Assay systems that not only facilitate the evaluation of a substance on cell viability, but also permit high throughput screens that can rapidly test thousands of compounds, streamline new drug discovery.

In clinical settings, diagnostic tests on large numbers of samples are facilitated when simple, accurate and safe assays are used. Disease treatments can then be more readily determined and instituted.

With the availability of whole genome sequences, the identification of gene products that affect ATP production, either indirectly or directly, is made possible, and high throughput screens to identify such proteins are facilitated by simple, fast, accurate and reliable ATP assays.

ATP assays are valuable for innumerable types of measurements for which it is important to determine the presence or absence of microbes or to determine the amount of microbial contamination present, e.g., determining microbial contamination of end products, hygiene monitoring, effectiveness of biocides, success of biological waste treatment processes, and the like.

ATP assays depend on reporter molecules or labels to qualitatively or quantitatively monitor ATP levels. Reporter molecules or labels in such assay systems have included radioactive isotopes, fluorescent agents, and enzymes, including light-generating enzymes such as luciferase. Desirable characteristics of any reporter molecule systems include safe, quick and reliable application and detection. Luminescent systems are among the most desirable since they are exceptionally safe and sensitive.

Light-generating enzymes have been isolated from certain bacteria, protozoa, coelenterates, mollusks, fish, millipedes, flies, fungi, worms, and crustaceans. Those enzymes isolated from beetles, particularly the fireflies of the genera *Photinus*, *Photuris*, and *Luciola*, and from click beetles of genus *Pyrophorus*, have found widespread use in reporter systems. In many of these organisms, enzymes such as luciferases catalyze oxido-reductions in which the free energy change excites a substrate molecule to a high-energy state. When the excited molecule returns to the ground state, visible light is emitted, i.e. "bioluminescence" or "luminescence." Among the assay systems in which bioluminescence has been employed to monitor or measure ATP are those in which the activity of an ATP-dependent bioluminescent enzyme, e.g. a beetle luciferase, is exploited.

When luciferase is combined with a sample for the purpose of detecting ATP, it is typically desirable to inhibit ATPases endogenous to the sample as well as enzymes that generate ATP, thus assuring that the ATP detected corresponds to the actual amount of ATP in a sample at a desired time. Many ATPase inhibitors are known, including detergents, especially detergents that are positively charged. However, most ATPase inhibitors are effective in not only eliminating ATPase function endogenous to the sample (e.g., a cell or cell population), but also ATPases that may be used as the reporter molecule, such as luciferase. Additionally, to counter ATP production, inhibitors of enzymes that phosphorylate, such as kinases, are desirable. However, these inhibitors, such as sodium fluoride (NaF), might also affect luciferase function. A challenge to improving ATP detection in a sample using luciferase depends on methods or compositions that substantially decrease or eliminate ATPase activity and ATP-generating activity endogenous to the sample, thereby stabilizing the amount of ATP present in the sample to that present when the composition is added, without confounding luciferase function.

There are multiple variations of cellular ATP detection methods currently used, all of which act in a stepwise manner. Some such methods first lyse the cells and inactivate the ATPase activity endogenous to the sample (e.g., by increasing sample pH), then neutralize the ATPase inhibitor, thereby converting the environment of the sample to one favorable to luciferase activity prior to adding the luciferase and detecting luminescence. Other such methods combine the neutralization of the ATPase inhibitor with the addition of luciferase. There are no ATP detection systems that provide a composition or method capable of inactivating endogenous ATPase activity and detecting luciferase activity in the same environmental milieu. Therefore, current assays that use luminescence to detect ATP are handicapped by the need for successive, time-consuming steps.

The present invention provides compositions with properties of enhanced stability comprising a luciferase and one or more ATPase inhibitors and further provides methods using these novel compositions to detect ATP in a sample by reducing the steps of cell lysis, endogenous ATPase inhibition, and substrate and luciferase addition to a single step that is then followed by detection of luminescence. Because embodiments of the invention significantly reduce the time and effort of luciferase-mediated detections of ATP by eliminating the need to neutralize ATPase inhibitor activity before adding luciferase, high throughput assays can finally be efficiently realized.

SUMMARY OF THE INVENTION

The invention is drawn to methods, compositions and kits that are used to detect and quantify ATP levels in a sample. The method comprises adding to a sample a composition ("reagent composition") comprising a luciferase enzyme and an ATPase inhibitor, and detecting luminescence produced in the sample by the conversion of a substrate into a luminescing compound by luciferase. The reagent composition has properties of enhanced stability, thereby eliminating the traditional step of inhibiting ATPases endogenous to a sample before adding luciferase enzyme to the sample. Thus, although luciferase functions as an ATPase, while in the reagent composition it is resistant to the effects of an ATPase inhibitor also present in the reagent composition. Such stable reagent compositions facilitate many ATP detections in a sample over a long period of time as well as detection of ATP in many samples over a long period of time.

In general, the methods comprise adding a composition ("reagent composition") comprising a luciferase (such as exemplified by, but not limited to, SEQ ID NOs: 1-4) and one or more ATPase inhibitors to a sample and detecting luminescence, where the activity of the reagent composition has enhanced stability [i.e., the reagent composition is capable of maintaining at least about 30%, more preferably at least about 60% activity (as measured by luminescence when the reagent composition is combined with the sample) for at least one hour, even more preferably at least 70%, 80%, 90%, 95%, 99% or greater activity for at least one hour, still more preferably for at least two hours and even more preferably for at least four hours relative to the reagent composition's activity when it is created, i.e., just after (0 to 10 minutes) the luciferase enzyme is combined with an ATPase inhibitor], and where the ATPase inhibitor is present in the reagent composition at a concentration sufficient to reduce ATPase activity endogenous to the sample by at least about 25%, more preferably at least about 30%, more preferably at least about 40%, even more preferably 50%, 60%, 70%, 80%, 90%, 95%, or 99% or greater relative to the sample's ATPase activity in the absence of the ATPase inhibitor. The reagent composition may be admixed before use by adding a solution comprising one or more ATPase inhibitors to a lyophilized luciferase.

Loss of stability is defined as irreversible loss of activity. The reagent composition loses stability over time and the amount of activity lost varies depending on the particular luciferase, ATPase inhibitor and, when present, enzyme stabilizing agent used. Preferably the stability of the reagent composition is demonstrable in the temperature range of about 20° C. to about 37° C. Although the methods of the invention may be used with a sample containing any amount of ATP, it is preferable to use a sample containing a non-saturated amount of ATP (i.e., a range where luminescence is linearly proportional to the concentration of ATP).

The luminescence generated by a luciferase reaction is typically detected with a luminometer although other detection means may be used. The presence of light greater than background level indicates the presence of ATP in the sample. The background level of luminescence is typically measured in the same matrix in which the sample exists, but in the absence of the sample. Suitable control reactions are readily designed by one of skill in the art. Preferred luciferases used in the compositions and methods of the invention generate a stable signal, i.e., they yield enhanced duration of luminescence in a luciferase reaction defined as less than 50% loss of luminescence per hour relative to the luminescence at the time the luciferase reaction was initiated. Preferred luciferases of the invention allow for multiple analyses of a sample over time or analysis of many samples over time, one hour after the luciferase is combined with the ATPase inhibitor, more preferably two hours and most preferably four hours or more. Optionally, the luciferases used in the compositions and methods of the invention have enhanced thermostability properties.

Quantifying the amount of emitted light also quantifies the amount of ATP in a sample, and thereby the quantity of living cells. Quantitative ATP values are realized, for example, when the quantity of light emitted from a test sample is compared to the quantity of light emitted from a control sample or to a standard curve determined by using known amounts of ATP and the same luciferase, substrate, and reaction conditions (i.e. temperature, pH, etc.). It is understood that quantification involves subtraction of background values. Qualitative ATP values are realized when the luminescence emitted from one sample is compared to the luminescence emitted from another sample without a need to know the absolute amount of ATP present in the samples, e.g., a comparison of samples in the presence or absence of a test compound. Many such experiments can readily be designed by one of ordinary skill in the art.

Examples of ATPase inhibitors include detergents, preferably detergents with charged groups such as cationic detergents [e.g., DTAB (dodecyltrimethylammonium bromide), CTAB (cetyltrimethylammonium) and BDDABr (benzyldimethyldodecylammonium bromide)], anionic detergents (e.g., SDS and deoxycholate), and zwitterionic detergents (e.g., sulfobetaine 3-10). To facilitate the method, a substrate for the luciferase, such as luciferin, may be included in the reagent composition. Other embodiments of the reagent composition further comprise a compound, such as NaF, that prevents an increase in ATP levels in the sample over time. Other compounds that prevent an increase in ATP levels in the sample include vanadate and paranitrophenylphosphate. Still other embodiments of the reagent composition further comprise a buffer and magnesium. One of skill in the art knows that other cations, such as manganese and calcium, may be suitable substitutes for magnesium.

The reaction composition may also comprise an enzyme stabilizing agent. The enzyme stabilizing agent can be any compound that stabilizes the luciferase from degradation.

Suitable enzyme stabilizing agents include proteins (such as bovine serum albumin or gelatin) or detergents (preferably non-ionic detergents, most preferably THESIT®).

Because the presence of ATP (or a particular ATP:ADP ratio) is a property of living cells, the invention is also directed to detecting and quantifying live cells in a sample using the above-described compositions. The amount of luminescence then correlates to the number of viable cells within a population, usually measured by lysing an aliquot of a population of cells of interest while applying the invention or extracting the ATP from a cell or population of cells.

Further, the present invention is useful for determining the effect of small molecules (including organic and inorganic molecules and synthetic and naturally occurring molecules) on living cells, which in turn allows the assessment of whether the small molecule may function as a pharmaceutical. Thus, the invention is also directed to methods that determine the effect of a compound on a first population of cells by contacting the first population of cells with a concentration of the compound and then at a later time contacting the first population of cells with a composition of the invention, detecting and comparing the amount of luminescence in the first population to an amount of luminescence in a second population of cells. The second population of cells may be contacted with a concentration of the compound that is less than the concentration contacting the first population of cells or with no compound. A lesser amount of luminescence detected from the first population compared to the second population may indicate that the compound comprises a cytotoxic agent. In this way, cytotoxic reagents may be discovered. Similarly, the invention is useful for discovering cell proliferation reagents, i.e., compounds that stimulate cell growth. Using the above example, a lesser amount of luminescence detected from the second population compared to the first population may indicate that the compound comprises a cell proliferation agent. The invention is useful for comparing the effects of different compounds at the same concentration on cells. The invention is also useful for comparing the effect of a compound on different types of cells. One of skill in the art may develop many other such assays for which the invention is useful.

The invention also assembles the elements of the invention into kits. Such kits are designed to determine the presence of ATP in a sample, e.g. measuring cell viability within a population of cells, or determining the effects of compounds on cells. Kits can be multifunctional such that more than one purpose can be realized. In one embodiment, a kit that is used to detect ATP in a sample may comprise lyophilized luciferase in one container, while another container contains reconstitution buffer with one or more ATPase inhibitors. The ATPase inhibitors may be detergents, preferably detergents with ionic groups including cationic detergents (preferably DTAB or BDDABr), anionic detergents (preferably SDS or deoxycholate) or zwitterionic detergents (preferably sulfobetaine 3-10) or a combination thereof.

The kit may also supply a luciferase substrate, such as luciferin. The kit may also supply magnesium or other cations such as manganese or calcium. To facilitate the use of control experiments with known concentrations of ATP, such as in embodiments of the kits that are used to quantify ATP in a sample, a container that has ATP may also be supplied in such kits. The kit may also supply a compound that prevents an increase in the amount of ATP in the sample over time (e.g., NaF). The kit may also supply a cell-lysing agent or an ATP extracting agent (e.g., TCA, DMSA, CTAB, ethanol, and the like). The kit may also supply a buffer. The kit may also supply an enzyme stabilizing agent, e.g., BSA or gelatin or THESIT®.

A preferred embodiment of the kit contains components which, when combined, generate a reagent composition that (i) maintains at least about 30% (preferably at least about 60%, even more preferably at least 70%, 80%, 90%, 95%, 99%) activity for at least about one hour (preferably at least two hours, more preferably four hours), as detected by luminescence when the reagent composition is combined with a sample, and relative to the reagent composition's activity just after it is assembled (i.e., 0 to 10 minutes after the component comprising luciferase is combined with the component comprising an ATPase inhibitor) and (ii) reduces at least about 25% or at least about 30%, (preferably at least about 40%, even more preferably at least about 50%, 60%, 70%, 80%, 90%, 95%, 99% or any increment therein) of the ATPase activity that is endogenous to the sample relative to the sample's ATPase activity in the absence of the ATPase inhibitor.

The component comprising an ATPase inhibitor may comprise greater than one ATPase inhibitor where they are present in the reagent composition at a concentration such that their combined effect reduces at least about 25% or at least about 30%, (preferably at least about 40%, even more preferably at least about 50%, 60%, 70%, 80%, 90%, 95%, 99% or any increment therein) of the ATPase activity that is endogenous to the sample relative to the sample's ATPase activity in the absence of the ATPase inhibitor and when allow for the reagent composition.

Most preferably the kit comprises a container comprising a buffered detergent solution, said buffered detergent solution at a pH in the range of about pH 6.0 to about pH 8.0, and said buffered detergent solution comprising DTAB whose concentration in the reagent composition is in the range of about 0.05% to about 2% (w/v) and optionally comprising NaF whose concentration in the reagent composition is in the range of about 1 mM to about 20 mM and optionally comprising THESIT® whose concentration in the reagent composition is in the range of about 1% to about 5%. The kit additionally comprises a separate container comprising lyophilized luciferase, preferably a luciferase with the sequence of SEQ ID NOs.: 1, 2, 3, or 4, most preferably SEQ ID NOs.: 2 or 4. Preferably the luciferase, when combined with the buffered detergent solution creating the reagent composition, is at a concentration of 1 μg/ml or greater, more preferably at a concentration of 80 μg/ml or greater. Preferably, the container comprising lyophilized luciferase further comprises lyophilized luciferin. Optionally, the kit further comprises instructions for use of the kit for the purpose of measuring ATP.

DETAILED DESCRIPTION OF THE INVENTION

Figure 1:
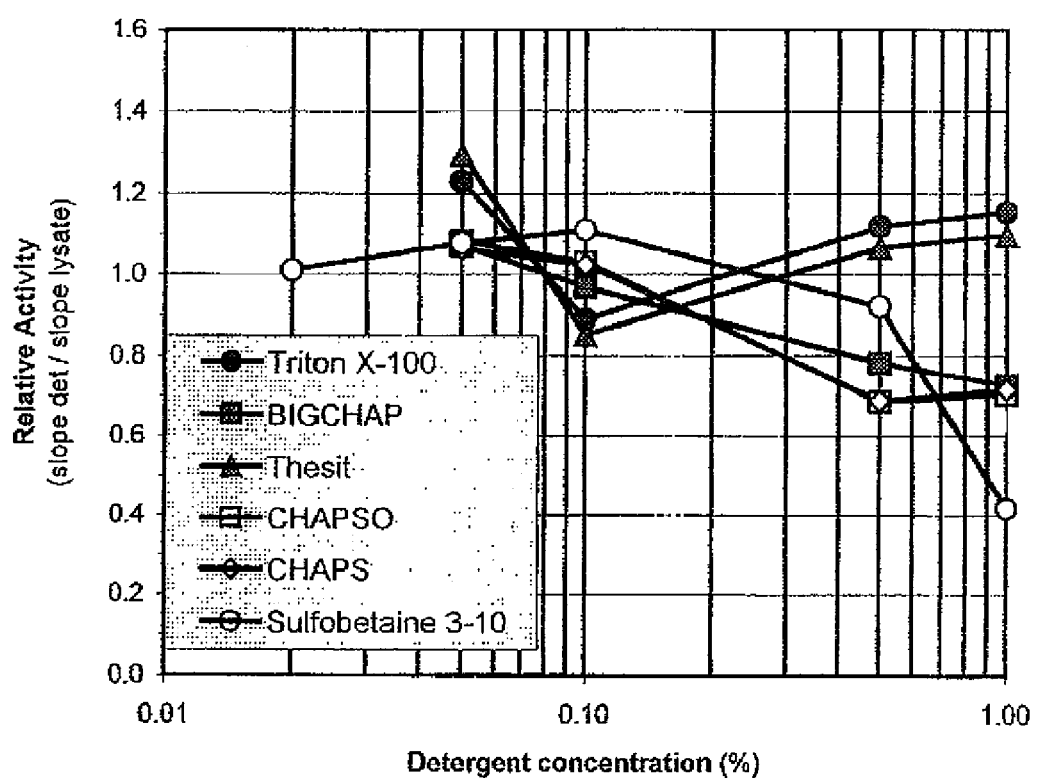
FIG. 1 is a graph illustrating the effect of increasing concentrations of various nonionic and zwitterionic detergents on relative ATPase activity in a sample.

The present invention provides compositions with properties of enhanced stability comprising a luciferase and one or more ATPase inhibitors. The invention further provides compositions with properties of enhanced stability comprising a cell lysing agent, a luciferase and one or more ATPase inhibitors. The invention further provides methods using these novel compositions to detect ATP in a sample by reducing the steps of cell lysis, endogenous ATPase inhibition, and substrate and luciferase addition to a single step that is then followed by detection of the resulting luminescence. Alternatively, cell lysis may be replaced with extraction of ATP from a cell or a population of cells. Preferably the luminescence resulting from the combination of a composition of the invention with a sample has an extended duration, i.e., diminished by less than about 50% per hour relative to the luminescence just after the composition is combined with the sample. The process of the invention significantly reduces the time and effort of luciferase-mediated detection of ATP in a sample by eliminating the need to neutralize ATPase inhibitor activity before adding luciferase.

There are multiple variations of ATP detection methods currently used, all of which act in a stepwise manner. Some such methods first lyse the cells and inactivate the ATPase activity endogenous to a sample (e.g., by increasing sample pH), and then neutralize the ATPase inhibitor, thereby converting the environment of the sample from one favoring ATPase inhibition and unfavorable to luciferase activity to one favorable to luciferase activity prior to adding luciferase and measuring luminescence. Similar methods exist in which the environment of the sample is converted to one favoring luciferase activity at the same time that the luciferase enzyme is added. There are no ATP detection systems that provide a composition or method capable of inactivating endogenous ATPase activity and allowing for luciferase activity in the same environmental milieu. And there are no ATP detection systems that provide a composition or method capable of lysing cells or extracting cellular ATP, inhibiting ATPase activity endogenous to a sample and allowing for luciferase activity in the same environment. Therefore, current assays that use luminescence to detect ATP are handicapped by the need for successive, time-consuming steps.

In preferred embodiments, the present invention reduces to a single step the manipulations needed for ATP detection in a sample, prior to luminescence measurement. In the single-step ATP assay of the invention, all of the necessary components of the ATP-dependent enzyme (e.g., luciferase), such as the enzyme, substrates, and ATPase inhibitors are comprised within a reagent composition and are added to a sample at once. In some embodiments the reagent composition further comprises a cell lysing agent or an agent for ATP extraction from cells. In some embodiments, a component of the reagent composition is a compound (e.g., NaF) that prevents an increase in ATP levels in the sample over time. The mechanism by which ATP levels are increased over time in certain samples, such as a cell lysate prepared with lymphoid cells (e.g., Jurkat cells), is not well understood, but it possibly results from the activity of a kinase enzyme endogenous to the sample. In some embodiments, a component of the reagent composition is an enzyme stabilizing agent.

A. DEFINITIONS

Unless defined otherwise, all technical and scientific terms have the same meaning as is commonly understood by one of skill in the art to which this invention belongs. All cited patents and publications are incorporated by reference in their entirety unless otherwise noted.

The nomenclature recommendations of Demerec et al., 1966, where these are relevant to genetics, are adapted herein. To distinguish between genes (and related nucleic acids) and the proteins that they encode, the abbreviations for genes are indicated by italicized (or underlined) text while abbreviations for the proteins start with a capital letter and are not italicized. Thus, luc or luc refers to the luciferase nucleotide sequence that encodes luciferase polypeptide or Luc.

An "isolated" or "purified" luciferase is one that has been identified and separated and/or recovered from a component of its natural environment.

The term "sample" as used herein, is used in its broadest sense. A sample is a composition suspected of containing ATP that is analyzed using the invention. While often a sample is known to contain or suspected of containing a cell or a population of cells, optionally in a growth media, or a cell lysate, a sample may also be a solid surface, (e.g., a swab, membrane, filter, particle), suspected of containing an attached cell or population of cells. It is contemplated that for such a solid sample, an aqueous sample is made by adding the solid to the reagent composition of the invention or to another aqueous solution to which the reagent composition of the invention is added. Filtration is desirable in some cases to generate a sample, e.g., in testing a liquid or gaseous sample by a process of the invention. Filtration is preferred when a sample is taken from a large volume of a dilute gas or liquid.

The term "detection," as used herein, refers to quantitatively or qualitatively determining the presence or absence of a component within the sample.

"Percent (%) amino acid sequence identity" is defined as the percentage of amino acid residues in one sequence that are identical to, with, or against amino acid residues in a second sequence in the region of overlap when the two sequences are optimally aligned. To determine percent amino acid identity, sequences are locally aligned and if necessary, gaps are introduced to achieve the maximum percent sequence identity; conservative substitutions are not counted when calculating sequence identity. Amino acid sequence alignment procedures to determine percent identity are well known to those of skill in the art. Publicly available computer software such as BLAST software (NCBI at www.ncbi.nlm.nih.gov/BLAST/) may be used to align peptide sequences. Those skilled in the art can determine appropriate algorithms and parameters for measuring alignment, including any algorithms and parameters needed to achieve optimal alignment of two amino acid sequences.

When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as:

$$\text{\% amino acid sequence identity} = (X/Y) \cdot 100$$

where X is the number of amino acid residues scored as identical matches in the optimal alignment of A and B by the sequence alignment program or algorithm and Y is the total number of amino acid positions aligned.

B. REAGENT COMPOSITION

The reagent composition of the present invention comprises one or more ATPase inhibitors, preferably a detergent, and a non-endogenous ATP-dependent enzyme, where the composition is capable of maintaining at least about 30% enzymatic activity for at least about one hour, preferably at least about 2 hours, more preferably at least about 4 hours, compared to its activity just after (0 to 10 minutes) the enzyme is combined with the ATPase inhibitor, and where the one or more ATPase inhibitors are present in the composition at a concentration sufficient to collectively reduce ATPase activity endogenous to the sample by at least about 25%, more preferably at least about 30%, 40%, 50%, 60%, 70%, 80%, 90%, 95% or 99% or any increment therein relative to the ATPase activity endogenous to the sample in the absence of the ATPase inhibitor. In preferred embodiments of the invention, the non-endogenous ATP-dependent enzymes are luciferases.

1. Luciferases

Luciferase enzymes whose catalytic products include light, offer sensitivity, a detectable product, and enable easy measurement of ATP. However, any luminescence-producing enzyme that is ATP-dependent may be used in the methods and compositions of the present invention.

At their most basic level, luciferases are defined by their ability to produce luminescence. More specifically, a luciferase is an enzyme that catalyzes the oxidation of a substrate, luciferin, thereby producing oxiluciferin and photons.

To date, five classes of luciferases have been identified (Jones et al., 1999; Thomson et al., 1997). Of these, beetle luciferases, such as that of the common firefly (family Lampyridae), form a distinct class with unique evolutionary origins (McElroy et al., 1969; White et al., 1969; White et al., 1975). Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art (Baldwin and Green, 2000; Beny and Dolivo, 1976; Branchini et al., 1980; Filippova et al., 1989).

Beetle luciferases, particularly firefly luciferase from the North American firefly *photinus pyralis*, are well known in the art. The *P. pyralis* luciferase (LucPpy) consists of approximately 550 amino acids of $M_r$ 61 kDa as calculated by the protein encoded by the nucleotide sequence of the gene. However, other firefly luciferases are desirable, such as *Photuris pennsylvanica* firefly luciferase (LucPpe2; 545 amino acid residues; GenBank 2190534, (Ye et al., 1997)). Mutant luciferases derived from LucPpe2 (e.g., LucPpe2m78 (also known as 78-0B10), SEQ ID NO.:1; LucPpe2m90 (also known as 90-1B5), SEQ ID NO.:2; LucPpe2m133 (also known as 133-1B2), SEQ ID NO.:3; LucPpe2m146 (also known as 146-1H2), SEQ ID NO.:4) are preferred; however, any luciferase that meets the limitations set forth herein may be used in the composition, method and kits of the invention. The method of making LucPpe2m78, LucPpe2m90, LucPpe2 ml 33, and LucPpe2m146 is disclosed in PCT/US99/30925.

Isolated and/or purified luciferases are typically used in the present invention. Contaminant components of its natural environment are materials that would typically interfere with diagnostic or therapeutic uses for the luciferase, and may include enzymes, hormones, and other proteinaceous or non-proteinaceous materials. One technique to ascertain purity is applying SD S-PAGE analysis under non-reducing or reducing conditions using Coomassie blue or silver stain. Isolated luciferase includes luciferase in situ within recombinant cells, since at least one component of the luciferase natural environment will not be present. Luciferases can be isolated from biological specimens that produce luciferase or from a cell that expresses an exogenous polynucleotide encoding a desired luciferase (e.g., a nucleotide encoding 78-0B10, 90-1B5, 133-1B2, or 146-1H2 (SEQ ID NOs.: 5-8, respectively)). Such techniques are well known to those of skill in the art.

The naturally-occurring substrate for beetle luciferases is firefly luciferin, a polytherocyclic organic acid, D-(−)-2-(6'-hydroxy-2'-benzothiazolyl)-$\Delta^2$-thiazolin-4-carboxylic acid (luciferin). Luciferin may be isolated from nature (e.g. from fireflies) or synthesized. Synthetic luciferin can have the same structure as the naturally occurring luciferin or can be derivatized, so long as it functions analogously (Bowie et al., 1973; Branchini, 2000; Craig et al., 1991; Miska and Geiger, 1987; Yang and Thomason, 1993). Examples of derivatives of luciferin include D-luciferin methyl ester, D-luciferyl-L-phenylalanine, D-luciferyl-L-N α-arginine, D-luciferin-O-sulphate and D-luciferin-O-phosphate (Miska and Geiger, 1987), esters of luciferases that are hydrolyzed or acted upon by esterases to luciferin by components in a sample (Craig et al., 1991; Yang and Thomason, 1993). Other examples of useful luciferin analogs include naphthyl- and quinolylluciferin, which emit light in the green and red light spectra respectively (Branchini et al., 1989). There are multiple commercial sources for luciferin (e.g., Promega Corp., Madison, Wis.; Molecular Probes, Eugene, Oreg.).

The beetle luciferase-catalyzed reaction that yields luminescence (the luciferase-luciferin reaction) involves firefly luciferin, adenosine triphosphate (ATP), magnesium, and molecular oxygen. In the initial reaction, the firefly luciferin and ATP react to form luciferyl adenylate with the elimination of inorganic pyrophosphate. The luciferyl adenylate remains tightly bound to the catalytic site of luciferase. When this form of the enzyme is exposed to molecular oxygen, the enzyme-bound luciferyl adenylate is oxidized to yield oxyluciferin in an electronically excited state. The excited oxidized luciferin emits light on returning to the ground state:

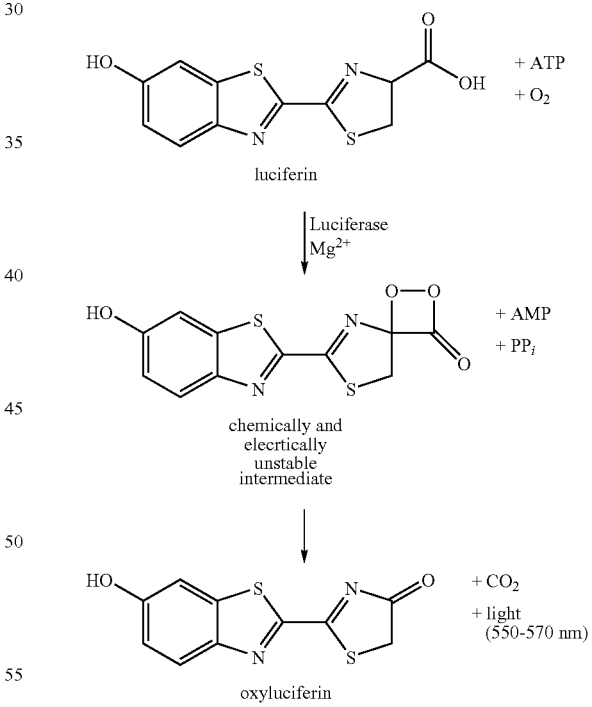

It is contemplated that the ATP function of the reaction can be performed by an ATP analogue (e.g., dATP). It is also contemplated that other ions can serve as substitutes for magnesium ions (e.g., $Mn^{2+}$ or $Ca^{2+}$). Additionally, oxygen is a reactant of the reaction. Therefore, the reaction should not be conducted under anaerobic conditions. However, it is not generally necessary in practicing the invention to provide oxygen over and above that present in the air. Reactions can take place in closed vessels, provided there is sufficient oxygen in the reaction solution.

Most luciferase-luciferin reactions generate a flash of light that is short-lived. However, some of the luciferases preferred for use with the invention, e.g., LucPpe2m146 and LucPpe2m90 luciferases, under the conditions of the invention generate a "glow-type" luminescent signal with less than 50% loss of luminescence per hour after the reagent composition is combined with the sample.

Any luciferase, luciferase variant, luciferase fragment, or variant luciferase fragment that retains the ability to generate luminescence when used in the reagent composition of the present invention and does not prevent the reagent composition from meeting the stability requirements of the present invention, can be used in the present invention.

A full length luciferase variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native luciferase sequence and retain the ability to generate luminescence. Ordinarily, variant luciferase fragments are at least about 50 amino acids in length, often at least about 60 amino acids in length, more often at least about 70, 80, 90, 100, 150, 200, 300, 400, 500 or 550 amino acids in length, or more, and retain the ability to generate luminescence. A luciferase, luciferase fragment, luciferase variant or variant luciferase fragment may be fused to other non-luciferase amino acid sequences and still be functional in the invention.

Full length beetle luciferase, fragments of beetle luciferase, variants of beetle luciferase, and variant fragments of beetle luciferase enzyme used in the compositions and methods of the present invention may be purified from a native source or prepared by a number of techniques, including (1) chemical synthesis, (2) enzymatic (protease) digestion of luciferase, and (3) recombinant DNA methods. Chemical synthesis methods are well known in the art, as are methods that employ proteases to cleave specific sites. To produce segments of luciferase protein, segments of luciferase or luciferase variants can be made and then expressed in a host organism, such as E. coli. Methods such as endonuclease digestion or polymerase chain reaction (PCR) allow one of skill in the art to generate an unlimited supply of well-defined fragments. Preferably, luciferase fragments share at least one biological activity with native luciferase, as well as catalytic activity, although the level of activity may vary from that of the native luciferase.

Any type of amino acid substitution, insertion or deletion, or combination thereof may be used to generate a variant luciferase. However, a luciferase with a conservative amino acid substitution is more likely to retain activity. Useful conservative substitutions are shown in Table A "Preferred substitutions." Conservative substitutions whereby an amino acid of one class is replaced with another amino acid of the same type fall within the scope of the invention if the substitution does not impair luciferase activity.

TABLE A

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |

TABLE A-continued

| Preferred substitutions | | |
|---|---|---|
| Original residue | Exemplary substitutions | Preferred substitutions |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect (1) the structure of the polypeptide backbone, such as a β-sheet or α-helical conformation, (2) the charge or (3) hydrophobicity, or (4) the bulk of the side chain of the target site might modify luciferase function. Residues are divided into groups based on common side-chain properties as denoted in Table B. Non-conservative substitutions entail exchanging a member of one of these classes for another class.

TABLE B

| Amino acid classes | |
|---|---|
| Class | Amino acids |
| Hydrophobic | Norleucine, Met, Ala, Val, Leu, Ile |
| neutral hydrophilic | Cys, Ser, Thr |
| Acidic | Asp, Glu |
| Basic | Asn, Gln, His, Lys, Arg |
| disrupt chain conformation | Gly, Pro |
| Aromatic | Trp, Tyr, Phe |

Variant luciferase genes or gene fragments can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce the luciferase variant DNA (Ausubel et al., 1987; Sambrook, 1989).

2. Preferred Luciferases

Preferred luciferases of the invention possess catalytic activity that depends on ATP and emits photons. Preferred luciferases of the invention have enhanced chemostability in the presence of ATPase inhibitors relative to the level of the P. pyralis luciferase (LucPpy) chemostability in the same reaction conditions. Preferred luciferases used in the compositions and methods of the invention generate a stable signal, i.e., they yield enhanced duration of luminescence in a luciferase reaction defined as a less than 50% loss of luminescence per hour relative to the luminescence at the time the luciferase reaction was initiated. Preferred luciferases of the invention allow for multiple analyses of a sample over time or analysis of many samples over time, one hour after the luciferase is combined with the ATPase inhibitor, more preferably two hours and most preferably four hours or more.

Optionally, the luciferases used in the compositions and methods of the invention have enhanced thermostability properties. An exemplified preferred luciferase is LucPpe2m146 (SEQ ID NO.:4). Additional examples of enzymes useful in the invention include, but are not limited to, LucPpe2m78 (SEQ ID NO.:1), LucPpe2m90 (SEQ ID NO.:2), and LucPpe2m133 (SEQ ID NO.:3).

The exemplified luciferases, LucPpe2m78 (SEQ ID NO.:1), LucPpe2m90 (SEQ ID NO.:2), LucPpe2m133 (SEQ ID NO.:3) and LucPpe2m146 (SEQ ID NO.:4) were generated from a mutant of *P. pennsylvanica* (T249M). The nucleic acid sequence encoding this protein was subjected to mutagenic methods including recursive mutagenesis followed by screens for thermostability, signal stability, and substrate binding and is fully described by Wood and Hall (WO 9914336, 1999).

Chemostability

"Chemostable luciferases" as used herein, defines luciferases that retain activity in the presence of compounds or conditions when those compounds or conditions typically inhibit ATPases and disrupt the function of non-chemostable luciferases such as LucPpy. The above-identified exemplary luciferases [(LucPpe2m78 (SEQ ID NO.: 1), LucPpe2m90 (SEQ ID NO.:2), LucPpe2m133 (SEQ ID NO.:3) and LucPpe2m146 (SEQ ID NO.:4)] were found herein to have enhanced chemostability to ATPase inhibitors.

Thus, preferred luciferases include those which maintain at least about 30% (preferably at least about 60%, 70%, 80%, 90%, 95%, 99%) enzymatic activity as measured by luminescence at least one hour (preferably at least two hours, more preferably at least four hours) after contact with an amount of ATPase inhibitor, preferably a detergent, e.g., cationic detergent preferably DTAB or BDDABr), anionic detergent (preferably deoxycholate or SDS) or zwitterionic detergent (preferably sulfobetaine 3-10) or combination thereof sufficient to collectively reduce ATPase activity endogenous to a sample by at least about 25% (preferably at least about 30%, even more preferably at least about 40%, 50%, 60%, 70%, 80%, 90%, 95%, 99% or any increment therein) relative to the sample's ATPase activity in the absence of the ATPase inhibitor.

The chemostability of an enzyme also may be indicated by the rate of decline of its activity over time. For example, shortly (0 to 10 minutes) after mixing the ATPase inhibitor and the luciferase, thereby creating the reagent composition, at several subsequent timepoints an aliquot of the reagent composition is added to a sample and relative light unit (RLU) measurements are obtained shortly thereafter. These measurements may be graphed to determine a trend of decline in enzyme activity in the reagent composition over time.

The preferred chemostable luciferases (e.g., Ppe2m78, Ppe2m90, Ppe2 m133, and Ppe2 m146) also retain activity in multi-detergent solutions. Specifically, solutions containing 0.01%, preferably 0.05%, 0.1%, 0.2%, 0.3%, 0.4%, 0.5%, 0.6%, 0.7%, 0.8%, 0.9%, most preferably 0.25% CHAPS (3-([3-Cholamidopropyl]dimethylammonio)-1-propanesulfonate) with at least 0.01%, preferably 0.05%, 0.1%, 0.2%, and most preferably 0.3% or 1.0% BDDABr, taurocholic or taurolithocholic acids, or DTAB, or 0.01%, preferably 0.05%, 0.1%, 0.2%, 0.3%, 0.4%, 0.5%, 0.6%, 0.7%, 0.8%, 0.9%, most preferably 1.0% of taurocholic or taurolithocholic acids with at least 0.01%, preferably 0.05%, 0.1%, 0.2%, and most preferably 0.3% or 1.0% BDDABr, DTAB, or CHAPS. Other multi-detergent solutions in which LucPpe2m78, LucPpe2m90, LucPpe2m133 and LucPpe2m146 retain activity include 0.01%, preferably 0.05%, most preferably 0.1% TRITON X-100 with at least 0.01%, preferably 0.05%, 0.1%, 0.2%, 0.5%, most preferably 1.0% BDDABr, DTAB, or CHAPS; or 0.01%, preferably 0.05%, 0.1%, 0.2%, 0.3%, 0.4%, 0.5%, 0.6%, 0.7%, 0.8%, 0.9%, most preferably 1.0% of taurocholic or taurolithocholic acids with at least 0.01%, preferably 0.05%, 0.1%, 0.2% and most preferably 0.3 or 1.0% BDDABr, DTAB, or CHAPS; or 0.05%, 1.0%, 2.0%, 4.0%, preferably 2% polyethylene glycol 400 dodecyl ether (THESIT®), with at least 0.05%, preferably 0.1%, 0.2% and most preferably 0.3% or 1.0% BDDABr, DTAB, or CHAPS.

Thermostability

In some embodiments, a thermostable luciferase that produces luminescence or other thermostable ATP-dependent enzyme that produces a detectable signal is desirable, especially in samples that are treated with heat immediately prior to ATP detection. A thermostable polypeptide remains active at temperatures that inactivate or denature other proteins. The LucPpe2m78, LucPpe2m90, LucPpe2m133 and LucPpe2m146 enzymes display increased thermostability compared to luciferases found in nature or encoded from polynucleotides isolated from nature.

Signal Stability

Preferred luciferases used in the compositions and methods of the invention generate a stable signal, i.e., such luciferases, when used in a luciferase reaction, yield luminescence with enhanced duration defined as less than 50% loss of luminescence per hour relative to the luminescence at the time the luciferase reaction was initiated. This property is referred to as signal stability. Preferred luciferases of the invention allow for multiple analyses of a sample over time or analysis of many samples over time, at least one hour after the luciferase is combined with the ATPase inhibitor, more preferably at least two hours and most preferably at least four hours or more. The combination of a luciferase and an ATPase inhibitor in the reagent composition, where the luciferase is capable of producing luminescence with enhanced duration while in the presence of an ATPase inhibitor (and, optionally, kinase inhibitors) that stabilizes the amount of ATP present in the sample results in a reliable and efficient method for detecting and quantifying cellular ATP for extended periods of time.

3. Other Desirable Luciferases

Any luciferase, luciferase fragment, or variants thereof that, in an ATP-dependent manner, emits photons upon oxidation of a substrate and is chemostable, i.e., retains activity in the presence of the ATPase inhibitors of the invention, may be used in the present invention. Other desirable characteristics, although not obligatory, such as thermostability and signal stability, are contemplated. In addition, the luciferase may be fused to another amino acid sequence and still be functional in the present invention. Such enzymes may be synthesized in vitro or isolated from other organisms.

Other luciferases are found in bacteria, unicellular algae, coelenterates, beetles (other than *P. pennsylvanica*), fish, and other organisms. Chemically, all luciferases involve exergonic reactions of molecular oxygen with different luciferins, resulting in photon production (Hastings, 1996; Hastings and Wilson, 1976; Wilson and Hastings, 1998; Wood et al., 1989). Preferably, other luciferases should be dependent on ATP for oxidation of luciferin, or the reaction conditions manipulated such that bioluminescence generation depends on ATP. One of skill in the art can ascertain ATP dependence for the luciferase-luciferin reaction.

The use of a luciferase other than that from beetles requires an appropriate luciferin molecule that upon oxidation generates a chemically and electrically unstable intermediate or a detectable enzymatic product. Other substrates may be used, as well as other ATP-dependent enzymes that produce a detectable enzymatic product. Detectable products include photons, radioactively-labeled products, insoluble or soluble chromogens, or other products that can be detected visually or through the use of devices.

C. KITS

When the invention is supplied as a kit, the different components of the composition may be packaged in separate containers and admixed prior to use. Such separate packaging of the components permits long-term storage without loss of luciferase-luciferin activity. However, when the various parts of the kit are admixed, thereby forming the "reagent composition," the reagent composition comprises a luciferase, such as exemplified by, but not limited to, SEQ ID NOs.:1-4, and one or more ATPase inhibitors where the activity of the reagent composition has enhanced stability [i.e., the reagent composition is capable of maintaining at least about 30%, more preferably at least about 60% activity for at least one hour, even more preferably at least 70%, 80%, 90%, 95%, 99% or greater activity for at least one hour, still more preferably for at least two hours and even more preferably for at least four hours (as measured by luminescence when the reagent composition is combined with a sample) relative to the reagent composition's activity when it is first created, i.e., 0 to 10 minutes after the luciferase enzyme is first combined with an ATPase inhibitor], and where the ATPase inhibitor is present in the reagent composition at a concentration sufficient to reduce ATPase activity endogenous to a sample by at least about 25%, more preferably at least about 30%, even more preferably at least about 40%, 50%, 60%, 70%, 80%, 90%, 95%, or 99% or greater relative to the ATPase activity in the absence of the ATPase inhibitor. Instructional materials may also be enclosed in the kit, as well as materials that may act as standards or controls, depending on the purpose of the kit.

1. The Reagent Composition

In a preferred embodiment, the components of the reagent composition of the invention can be supplied as two parts that are admixed shortly before use: (1) a part comprising luciferase and (2) a part comprising one or more ATPase inhibitors. An example of such an embodiment is represented in Table C and others are represented in the Examples. The luciferase component may further comprise luciferin and preferably is lyophilized. The luciferase component optionally comprises excipients for lyophilization, protein (luciferase) stabilizer, magnesium (or alternative cation), and a magnesium chelator (or alternative cation chelator). The ATPase inhibitor component may further comprise a buffer, divalent cation metal chelators, magnesium (or alternative cation), a defoaming agent, anti-ATP-generating enzyme agents (e.g., NaF), an enzyme stabilizer (e.g., THESIT®) and cell lysing agent or agent for extracting ATP from cells. The different components of the invention may comprise subsets of these parts and may be combined in any way that either facilitates the application of the invention or prolongs storage life.

TABLE C

Preferred components of a kit

| Component | Action | Preferred embodiments |
|---|---|---|
| Luciferase/luciferin | Catalyzes luciferase-luciferin reaction in one step | Ppe2m90 or Ppe2m146 luciferase |
| | Substrate | Luciferin |
| | Lyophilization excipient and protein stabilizer | Highly purified porcine dermal collagen (Prionex) |
| | Enzyme cofactor | $MgSO_4$ |
| | Chelates Mg after ATP removal | 1,2-Cyclohexanediaminetetraacetic acid (CDTA) |
| ATPase/Extraction | Buffer | Citrate buffer |
| | | Potassium Phosphate buffer |
| | Buffer | 2-(N-Morpholino)ethanesulfonic acid (MES) |
| | Chelates divalent metal cations | Ethylenediaminetetraacetic (EDTA) |
| | Defoamer | MAZU DF204 |
| | ATPase inhibitor | DTAB |
| | Inhibitor of ATP-generating activity | NaF |
| | Non-ionic detergent, disrupts cellular membranes | THESIT ®, Polyoxyethylene(9)-lauryl-ether |

2. Luciferase-Luciferin Component

All luciferases, luciferase variants, luciferase fragments and variant luciferase fragments that catalyze an ATP-dependent reaction and generate luminescence are contemplated for use in the invention. Some embodiments eliminate the luciferin; for example, allowing a user to supply a luciferin of his/her choice, or the luciferin may be provided separately. The type of luciferin provided may vary but it must be a substrate for the type of luciferase provided.

In one embodiment, a kit supplies the luciferase as an anhydrous preparation. Anhydrous preparations of luciferase may be lyophilized, in which water is removed under vacuum, freeze-dried, crystallized, or any other method that removes water that does not inactivate luciferase. Excipients that bulk the preparation and stabilize luciferase, such as serum albumins or Prionex, may also be included. In other embodiments, luciferase may be suspended in an aqueous composition comprising glycerol or other solvent in which the enzyme is stable. The skilled artisan can easily determine the amounts of the various constituents that work in the compositions and methods of the invention.

3. ATPase Inhibitor Component

In a preferred embodiment, the kit comprises a component containing one or more ATPase inhibitors within a solution optionally containing other functional components, such as buffers, defoamers, enzyme stabilizers, and the like. This component may be supplied as a working solution or as a concentrate. A cell lysing agent or an agent that allows for cellular ATP extraction (e.g., CTAB) may be packaged separately or together with the ATPase inhibitor component. The ATPase inhibitor may be any of those described herein above. This component may further comprise agents that chelate metal ions that may interfere with the luciferase-luciferin reaction (e.g. EDTA, EGTA), magnesium (preferably supplied as a salt, such as sulfate or chloride; or other functionally equivalent cation), defoaming agents, and inhibitors of ATP generating enzyme (e.g. NaF). Buffers that maintain pH of the working solution, e.g. citrate or MES (which may be supplied as a salt, such as sodium or free acid or base) or any other appropriate buffer may be used.

ATPase Inhibitor

One aspect of the invention is an ATPase inhibitor, preferably a detergent that inhibits ATPases, more preferably a detergent with a charged group, e.g., cationic detergent (preferably DTAB or BDDABr), anionic detergent (preferably deoxycholate or SDS) or zwitterionic detergent (preferably sulfobetaine 3-10). Such inhibitors prevent ATPases endogenous to the sample from processing ATP to adenosine diphosphate (ADP) and adenosine monophosphate (AMP) before the luciferase is allowed to utilize the ATP in the sample for the luciferase-luciferin reaction. ATPase inhibitors may inactivate ATPases directly or indirectly. They may bind to ATPases, either in the active sites, thus preventing substrate binding, or denature ATPases, such as by denaturing detergents, or they may selectively sequester ATPases from their substrates.

One embodiment of the present invention uses cationic detergents such as DTAB or BDDABr detergents that act as ATPase inhibitors. However, other ATPase inhibitors are contemplated, such as other cationic detergents, anionic detergents (e.g., SDS and deoxycholate) and zwitterionic detergents (e.g., sulfobetaine 3-10).

For DTAB or BDDABr the concentration in the reagent composition is preferably in the range of about 0.02% to about 5.0%, more preferably about 0.05%, still more preferably about 0.1%, 0.2%, 0.3%, 0.4%, 0.5%, 0.6%, 0.7%, 0.8%, 0.9%, 1.0%, 1.1%, 1.2%, 1.3%, 1.4% and 1.5% and most preferably to a final concentration of about 1.0% in the reagent composition.

Other non-cationic detergent ATPase inhibitors are contemplated for inclusion in the reagent composition; their requirements are that they, like DTAB, preferably inhibit at least about 25%, more preferably at least about 30%, 40%, 50%, 60%, 70%, 80%, 81%, 82%, 83%, 84%, 85%, 86%, 87%, 88%, 89%, 90%, still more preferably at least about 91%, 92%, 93%, 94%, 95%, 96%, 97%, 98%, 99% and most preferably about 100% of endogenous ATPase activity in a sample when present in a reagent composition where the reagent composition is capable of maintaining at least 30%, 40%, 50%, 60%, 70%, 80%, 81%, 82%, 83%, 84%, 85%, 86%, 87%, 88%, 89%, 90%, more preferably at least about 91%, 92%, 93%, 94%, 95%, 96%, 97%, 98%, 99% and most preferably about 100% activity, as measured by luminescence after the reagent composition is combined with the sample, for at least one hour, more preferably at least 2 hours compared to the reagent composition's activity just after the luciferase is combined with the ATPase inhibitor. Potentially suitable non-cationic detergents that function as ATPase inhibitors include anionic detergents (preferably SDS and deoxycholate) and zwitterionic detergents preferably sulfobetain 3-10). The concentration of a particular ATPase inhibitor will vary depending on the inhibitor used, and to some extent, the sample being analyzed. One of skill in the art is familiar with methods to determine the appropriate concentration of an ATPase inhibitor for inclusion in the reagent composition; for example, they may examine luciferin-luciferase derived signals over time, comparing those samples that have varying concentrations of a candidate ATPase inhibitor to those samples containing no known ATPase inhibitors.

It is fully anticipated that the most preferred concentration and even the concentration range functional in the methods of the invention will vary for different detergents. For example, SDS concentrations functional in the methods of the invention are about 0.002% (Examples 2 and 3). The functional concentration range for a detergent used in the present invention may readily be determined by one of skill in the art using the methods disclosed herein.

It is contemplated that some ATPase inhibitors, at some of the concentrations useful in the invention, may be insoluble or have low solubility in aqueous solutions. These compounds may first be dissolved in an organic solution (e.g., dimethyl sulfoxide or dimethylformamide) and then diluted into the reagent composition for use in the composition and methods of the invention.

Inhibitors of ATP-Generating Enzymes

In some samples, enzymes such as kinases may be active, allowing for continued production of ATP. Because the ATP concentration is determined at a specific time, if such enzymatic activity is left unchecked, then an overestimation of the ATP concentration will be made. To counter such ATP-generating activity, inhibitors of ATP production can be used. Although the action of a specific inhibitor may be incompletely understood, their usefulness is not obviated. Examples of useful compounds include NaF, which is useful at concentrations of at least 1 mM, preferably 2 mM to 100 mM or any increment therein; 2 mM is most preferred. Any such inhibitor may be used, however, if it does not adversely affect luciferase so as to take it outside the utility of the invention. One of skill in the art will know how to determine the appropriate concentration of such an inhibitor, whether the inhibitor is novel or well-known. Other inhibitors of ATP-generating enzymes include, but are not limited to, vanadate, paranitrophenylphosphate and dichloroacetic acid (Kiechle et al., 1980).

Buffers

Any buffers that maintain suitable pH for the working solution and do not interfere with the luciferase-luciferin reaction are contemplated. The preferred pH range is between about pH 4.5 and about pH 9.0, more preferably between about pH 6.0 and about pH 8.0. In addition to MES and citrate buffers, other buffers, such as phosphate buffered saline (PBS), Tris-N-(2-Hydroxyethyl)piperazine-N'-(2-ethanesulfonic acid) (HEPES), piperazine-1,4-bis(2-ethanesulfonic acid) (PIPES), borate, and any other buffer known to those of skill in the art may be suitable. Selection of appropriate buffers depends on pH buffering capacity and interaction with the luciferase-luciferin reaction.

Defoamers

Defoaming agents are desirable to prevent foam from interfering with the detection of bioluminescence, especially in applications that quantify luminescence. Such agents as MAZU may be organic or silicone based. Selection of defoamers depends on their ability to eliminate foam without interfering with the luciferase-luciferin reaction.

Magnesium

The beetle luciferase-luciferin reaction is dependent not only on ATP, but also on magnesium ions. To ensure luciferase activity, magnesium is exogenously supplied. In addition to magnesium sulfate, other salts of magnesium are contemplated, such as magnesium chloride, magnesium gluconate, magnesium acetate, magnesium bromide, magnesium carbonate, etc. In any case, the magnesium complex must dissociate to make $Mg^{2+}$ ions available to the luciferase and not interfere with the luciferase-luciferin reaction. One of skill in the art is aware that other cations may be functional in place of magnesium. These include calcium and manganese.

In some applications, endogenous magnesium should be sufficient, in which cases exogenous magnesium could be eliminated.

Cell Lysing Agents and ATP Extraction Agents

To free any sequestered ATP within a cell and to lyse cells in a sample, cell-lysing agents, such as non-ionic detergents, may be included. Any cell lysing agent is contemplated including other non-ionic detergents, (such as from the Triton series) cationic, anionic and zwitterionic detergents, bile salts, chaotropes, and any other agent that disrupts cellular membranes, including bacterial toxins such as oxylysins. Alternatively any agent that allows for ATP extraction from a cell is contemplated (such as CTAB). Agents that allow for ATP extraction from a cell include detergents present at a concentration that puts holes in the cell membrane, allowing for ATP within the cell to leach into the surrounding media, but not present at such a concentration that produces a cell lysate.

Stablizing Agents

While resistant to the action of nonionic and low concentrations of zwitterionic detergents (Simpson and Hammond, 1991), native firefly luciferase is inactivated by cationic detergents, such as benzalkonium chloride, benzethonium chloride, CTAB (cetyltrimethylammonium), DTAB (dodecyltrimethylammonium bromide), and methylbenzethonium chloride (Simpson and Hammond, 1991).

The stabilizing agent can be any compound that stabilizes the luciferase from degradation. Suitable stabilizing agents include proteins (such as bovine serum albumin or gelatin) or detergents (preferably non-ionic detergents, most preferably THESIT®).

Other Agents

Other agents that may be included in a kit include substances that are known to enhance the duration of luminescence resulting from a luciferase reaction, such as co-enzyme A (CoA), thiol reagents, such as dithiothreitol and β mercaptoethanol (Wood, U.S. Pat. No. 5,283,179, 1994; Wood, U.S. Pat. No. 5,650,289, 1997), metal ion chelators such as EDTA to prolong the signal and protease inhibitors (Scheirer, U.S. Pat. No. 5,618,682, 1997; Scheirer, U.S. Pat. No. 5,866,348, 1999), or high concentrations of salts (Van Lune and Trer Wiel, WO 00/18953, 2000).

Other Kit Contents

Kits may also include reagents in separate containers that facilitate the execution of a specific test, such as cell viability, cytotoxicity, cell proliferation, or determination of ATP concentration. For example, ATP may be supplied so that standard curves may be determined or for use as internal controls. Substances that are known to be cytotoxic to cells can be included for use as a positive control in tests of cell viability or for the effects of compounds on cells. The kit may supply a sample gathering component such as a membrane, filter or swab.

4. Containers or Vessels

The reagents included in the kits can be supplied in containers of any sort such that the life of the different components are preserved, and are not adsorbed or altered by the materials of the container. For example, sealed glass ampules may contain lyophilized luciferase or buffer that have been packaged under a neutral, non-reacting gas, such as nitrogen. Ampules may consist of any suitable material, such as glass, organic polymers (such as polycarbonate, polystyrene, etc., ceramic, metal or any other material typically employed to hold reagents. Other examples of suitable containers include simple bottles that may be fabricated from similar substances as ampules, and envelopes, that may have interiors lined with foil, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

5. Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail. In a preferred embodiment, the instructions instruct the user to combine the luciferase with the ATPase inhibitor before adding the reagent composition to a sample.

D. REAGENT COMPOSITION ACTIVITY

To measure luminescence and thereby determine the reagent composition activity, the relative light unit (RLU) value generated by the luciferase reaction at a timepoint of interest after the reagent composition is combined with a sample may be measured. For example, an RLU value may be obtained by measuring the resulting luminescence from a sample with a known concentration of ATP combined with the reagent composition just after (0-10 min) the component comprising the ATPase inhibitor is added to the component comprising the luciferase thereby creating the reagent composition. This is considered 100% activity (time zero) under those conditions. If, after combining the component comprising the ATPase inhibitor with the component comprising the luciferase and thereby generating the reagent composition, the reagent composition is left for two hours, preferably in the temperature range of room temperature (about 20° C.-about 25° C.) to about 37° C., prior to measuring luminescence under identical conditions as the time 0 assay, and the RLU value obtained is greater than 60% of that obtained at time 0, then the reagent composition retained at least 60% of its activity for two hours.

A reagent composition of the present invention retains 30%, 40%, 50%, 55%, 60%, 65%, 70%, 75%, 80%, 85%, 90%, 95%, 96%, 97%, 98%, 99% or any increment therein and most preferably 100% of its activity, as measured by luminescence after the reagent composition is combined with the sample for at least one hour, preferably for at least two hours, relative to its activity when formulated (time 0)—that is from the time the component comprising the ATPase inhibitor was added to the component comprising luciferase or shortly thereafter (0-10 minutes).

In one preferred embodiment, the working stock of the reagent composition comprises DTAB or BDDBr in concentrations of about 0.02% preferably about 0.05%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 5.5%, 6%, 6.5%, 7%, 7.5%, 8%, 8.5%, 9%, 9.5%, 10% and any increment therein, more preferably about 1%) and retains at least about 30% preferably at least about 40%, 50%, 60%, 70%, 80%, 90%, 95%, 99%) of activity at least one hour preferably at least two hours) after formulation.

In another preferred embodiment, the reagent compositions comprise sulfobetaine at a concentration of 0.6%, 0.7%, 0.8%, 0.9% or 1.0% or any increment therein, SDS at a concentration of 0.001%, 0.002%, 0.003%, 0.004% or 0.005% or any increment therein, or deoxycholate at a concentration of 0.1%, 0.2%, 0.3%, 0.4%, 0.5%, 0.6% or any increment therein and retain at least about 30% preferably at least about 40%, 50%, 60%, 70%, 80%, 90%, 95%, 99%) of activity at least one hour (preferably at least two hours) after formulation.

E. DETECTING AND QUANTIFYING THE PRODUCTS OF THE LUCIFERASE-LUCIFERIN REACTION

A beetle luciferase-luciferin reaction results in the generation of light ("luminescence"). The invention provides assays for ATP measurement by measuring luminescence. Users may simply visually inspect sample reactions to ascertain the production of light. However, more sensitive instrumentations allow not only detection of faint signals, but also quantification of the light signal. Also contemplated are reactions in which non-light products are measured, according to the nature of the products. Any assay for measurement of ATP that results in a signal may benefit from the present invention. Appropriate instruments and methods for such products will be apparent to the skilled artisan.

In all cases in which light is detected, specialized instruments, such as luminometers, can read the light product of a luciferase-luciferin reaction. Any instrument that can detect the light of the wavelengths emitted by the luciferase-luciferin reaction may be used. Such instruments may read samples singularly, or, in high-throughput screens, may read many samples housed in the wells of microwell plates (6, 24, 48, 96, 384, 1536 and so on, well formats). Clearly, the devices used to measure the emitted light do not limit the invention. Other devices that can be used include scintillation counters (Nguyen et al., 1988) or instruments invented or adapted to be sensitive to luminescence, such as photometers (Picciolo et al., 1977). Photographic film or X-ray film may also be used to detect luminescence. In addition, a user may visually inspect a sample to qualitatively evaluate luminescence.

F. USES FOR ATP-DEPENDENT LUCIFERASE-LUCIFERIN REACTIONS

Because the beetle luciferase-luciferin reaction is ATP-dependent, luciferase can be used to assay for ATP. The reaction is remarkably sensitive, allowing ATP to be detected in a sample containing as little as $10^{-16}$ moles ATP or less. This sensitivity can be exploited to understand cell viability and the effects that exogenous substances may exert on cell metabolism and viability. In a cellular context, ATP powers cellular metabolism, the presence of ATP correlates to an actively metabolizing cell, i.e. the cell is "viable."

The invention is drawn to methods, compositions and kits that are used to effectively and accurately detect and quantify cellular ATP levels, exploiting the ATP-dependence of beetle luciferase to oxidize luciferin.

The invention comprises the addition of a single composition (reagent composition) that comprises a luciferase and at least one ATPase inhibitor to a sample and the detection of luminescence. Optionally, a kinase inhibitor or a compound that prevents accumulation of ATP can also be present in the reagent composition. Additionally, a cell-lysing agent (e.g., a polyoxyethylene such as THESIT®) or an ATP extracting agent may be present in the composition. This single step comprising adding the reagent composition followed by reading the luminescence represents a significant advance in assays for ATP.

1. Detecting ATP

The methods, compositions and kits of the invention provide for the simple qualitative or quantitative detection of ATP (or ATP analogue which can function as a luciferase substrate) in a sample. In preferred embodiments, a simple qualitative experiment in which luminescence is generated in a sample using the invention, indicates the presence of ATP. Luminescence is generated using a reagent composition comprising luciferase such as LucPpe2m78, LucPpe2m90, LucPpe2m133 or LucPpe2m146, and one or more ATPase inhibitors. In addition, the reagent composition may further comprise one or more of the following components: luciferin, which may be reconstituted from a lyophilized preparation, (alternatively, an appropriate luciferin-analogue substrate), ATPase inhibitor(s), inhibitor(s) of ATP-generating enzymes such as kinases, divalent cation (e.g. magnesium), enzyme stabilizing agent, buffer, cell-lysis agent or cellular ATP extracting agent.

A sample may be anything that is suspected of containing ATP or ATP analogue, such as cell lysates, intact cells, biopsies, foods, beverages, swabs wiped on surfaces such as those of animals, plants, or inanimate objects, and the like. Other examples of samples include compositions of a known ATP concentration. Cells or cell lysates may be from any organism, prokaryotic or eukaryotic. Examples of prokaryotic cells include *E. coli, P. aeruginosa, B. subtilis,* and *S. typhimurium*. Eukaryotic cells may be from plants, animals, fungi, insects, etc. or cultured cells from such organisms. Examples include *A. thaliana* and *Brassica* sp., *Chlamydomonas* sp. and *Volvox* sp. (plants), *H. sapiens* and *Mus* Sp. (animals), *Saccharoymyces* sp. (esp. *cerevisae* and *pombe*) and *Neurospora* Sp. (fungi), *D. melanogaster* and *C. elegans* (insects), in vitro cultured callus cells from any plant, primary cells cultured in vitro from any organism (such as organ explants from, for example, rodents), mammalian cell lines such as Madin-Darby canine kidney (MDCK) and Chinese hamster ovary (CHO) cells, and insect cell lines such as Z cells. These examples are furnished only as examples and are not meant to be limiting.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents, such as those in which LucPpe2m146 retains activity, such as zwitterionic and nonionic detergents, or cationic detergents DTAB or CTAB. Preferably, the cell lysate is produced in such a way that the integrity of the ATP concentration is preserved at the time the cells are harvested. To accurately detect ATP in a sample, enzymes that would degrade cellular ATP or those that would generate ATP are preferably inhibited. In the absence of such inhibitors, an inaccurate determination of ATP concentration risks being made. Inhibitors such as DTAB inactivate ATPases, while other molecules such as NaF inactivate ATP-generating enzyme activity. It is hypothesized, yet not fully understood, that for those cell types in which NaF is effective (e.g., lymphoid cells), NaF is potentially acting to inhibit (a) kinase(s).

Inhibitors of ATP-generating enzymes, those enzymes that have as a product or by-product ATP, such as the activity of kinases, may be incorporated into the reagent composition. An example of an effective inhibitor is NaF (Bostick et al., 1982). Such compositions comprise NaF at concentrations of at least 0.5 mM, preferably at least 1 mM, more preferably at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 953, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mM or any increment therein; 2 mM is most preferred. Other inhibitors of ATP-generating enzymes include other kinase inhibitors, such as vanadate, AMP, DAPP (Bostick et al., 1982) and dichloroacetic acid (Kiechle et al., 1980).

2. Quantifying ATP

The compositions, methods and kits of the invention permit a user to quantify the amount of ATP in a sample by quantifying the amount of luminescence. The invention is applied to a sample of interest, and also to samples containing known amounts of ATP (controls). The signal generated from applying the invention to a sample of unknown ATP concentration is correlated to signals generated either by internal controls (the addition of a known amount of ATP to a sample and measuring the subsequent luminescence) or external standard curves, generated by measuring the luminescence of several samples of known ATP concentrations and plotting them graphically. Such methods are known to skilled artisans. (Moyer and Henderson, 1983; Ronner et al., 1999; Stanley, 1989; Wood et al., 1989).

3. Cell Viability

The presence of ATP in a cell, eukaryotic or prokaryotic, indicates active metabolic processes, indicating a viable cell. The compositions, methods and kits of the present invention can be used to assay cell viability (Cree, 1998; Jassim et al., 1990; Petty et al., 1995). An accurate measure of cell viability allows for the accurate assessment of the effects of substances on cells; other purposes for determining cell viability are well-known to those of skill in the art.

Determining cell viability is useful, for example, to determine cytotoxicity, cell proliferation, biological phenomena, necrosis, or alterations in cellular metabolism. Cell viability assays can also determine the overall viability of a cell population.

The sample in which ATP is measured to determine cell viability may be viable cells themselves, a cell lysate or any other sample suspected of containing cells. When using cells, modified beetle luciferases that are membrane permeable may be used (for example, see Craig et al., 1991). In many cases, however, a cell lysate is preferred.

4. Effects of Compounds on Cells

The compositions, methods and kits of the present invention can be applied to measure the effects of compounds, such as inorganics, small organics, peptides, proteins and polypeptides, on cellular metabolism when contacted with a sample (Aiginger et al., 1980; Andreotti et al., 1995; Bradbury et al., 2000; Cree and Andreotti, 1997; Crouch et al., 1993; Kangas et al., 1984). Determining the effects of compounds on cells can assess the measure of a potential pharmaceutical composition's effectiveness. Cytotoxic compounds—those that kill cells—can be useful in the treatment of cancer cells, especially if they selectively kill quickly-dividing cells. In other cases, a compound with some other usefulness may be negated if a cytotoxic effect is not desired. Because ATP is a measure of a cell's "metabolic" health, an abnormal surge or depression of ATP reduction indicates a change in cellular homeostasis. Compounds that contact cells can influence ATP production through a large number of mechanisms, most notably cell death and cell proliferation. These compounds may be catalogued in compound libraries, or tested singly. Such applications of the invention apply controls in which samples are contacted with control substances whose effects on ATP metabolism are known. Also preferably, controls include samples in which luciferase and the compound are present together to assure that the compound itself is not directly affecting luciferase activity.

The following examples are intended to illustrate the present invention without limitation.

EXAMPLES

Example 1

I. Detergents that Inhibit ATPases

This example was designed to test the ability of different detergents to inhibit ATPase activity endogenous to cells and demonstrate the level of such inhibition. Three separate detergents in each of four detergent classes were tested: anionic [SDS (Sodium dodecyl sulfate), Bioterge (an α olefin sulfate), and sodium deoxycholate], nonionic [TRITON X-100, BigCHAP (N,N-bis(3-D-Gluconamidopropyl)cholamide) and THESIT® (polyethylene glycol 400 dodecyl ether, Fluka, #88315)], cationic [BDDABr (Benzyldimethyldodecylammonium bromide), CTAB (Cetyltrimethylammonium bromide), and DTAB (dodecyltrimethylammonium bromide)] and zwitterionic [CHAPS (3-[(3Cholamidopropyl)dimethylammonio]propanesulfonic acid), CHAPSO (3-([3-Cholamidopropyl]dimethylammonio)-2-hydroxy-1-propanesulfonate), and Sulfobetaine 3-10 (N-Dodecyl-N,N-dimethyl-3-ammonio-1-propanesulfonate)]. Detergents were obtained from Sigma, Fluka and Aldrich.

L929 cells (ATCC CCL-1; $1.5 \times 10^5$ cells/ml) in F12/DMEM (Hyclone, SH130023) containing 10% horse serum (Hyclone, SH30074) were frozen and thawed for four cycles to create a cell lysate. Then 50 μl of stock detergent solutions [10%, 5.0%, 1.0%, and 0.5% (w/v)] were separately added to 450 μl cell lysate, creating a final detergent concentration in the cell lysate sample of 1.0%, 0.5%, 0.1%, and 0.05%, respectively (these percentage values are those used in Tables D and E herein below). Control samples contained either lysate only or 1.0 μM ATP in 15 mM HEPES buffer (pH 7.5). All samples were incubated at 22° C. (room temperature) for the duration of the experiment.

At various timepoints, 20 μl from each sample/detergent mixture was added to a 96-well luminometer plate in triplicate, and then 100 μl of a solution ("luciferase-luciferin" or "L/L reagent") containing 25 mM HEPES buffer (pH 7.5), 40 μg luciferase enzyme LucPpe2m146 (Promega, E140), 100 μM luciferin (Promega), and 10 mM $MgSO_4$ was added to each well. The L/L reagent was stored at 4° C. for the duration of the experiment and then allowed to reach ambient temperature just before assaying. After mixing the contents of the plate, light output was measured with a Dynex MIX microtiter plate luminometer (Chantilly, Va.), 0.5 second reads per well with the first measurement taken five minutes after the detergent solution was combined with the sample. The average relative light units and the timepoint at which it was measured (RLU; Table D) and percent of remaining luciferase activity at the timepoint (Table E) are reported;

controls were run with each set of experimental conditions as indicated. The cationic and anionic detergents were assayed on one day with one set of controls. The zwitterionic and nonionic detergents were assayed on a separate day with a separate set of controls. The DTAB at 0.5% was assayed on both days (1 and 2). If the original average RLUs reported in Table D were below 5.0, the percent of original activity values were not recorded in Table E as the detergent was determined to be present at a concentration that significantly destroyed luciferase activity.

TABLE D

| | Average Relative Light Unit Values | | | | |
|---|---|---|---|---|---|
| | 5 min | 75 min | 169 min | 222 min | 260 min |
| Controls | | | | | |
| Cell lysate (cationic and anionic) | 6713.33 | 1844.71 | 953.35 | 384.77 | 200.78 |
| Cell lysate (nonionic and zwitterionic) | 6748.77 | 2297.65 | 1212.43 | 508.38 | 246.19 |
| ATP Control (cationic and anionic) | 19986.2 | 16628.6 | 17439.9 | 20174.3 | 15668.7 |
| ATP Control (nonionic and zwitterionic) | 17779.6 | 18218.8 | 16639.6 | 18886.2 | 17952.2 |
| Anionic Detergents | | | | | |
| SDS | | | | | |
| 1.0% | 0.01 | 0.00 | 0.01 | 0.00 | 0.01 |
| 0.5% | 0.00 | 0.00 | 0.02 | 0.00 | 0.00 |
| 0.1% | 0.31 | 0.18 | 0.21 | 0.26 | 0.34 |
| 0.05% | 1181.17 | 1060.03 | 949.7 | 921.86 | 803.0 |
| Bioterge | | | | | |
| 1.0% | 0.01 | 0.01 | 0.01 | 0.01 | 0.02 |
| 0.5% | 0.1 | 0.04 | 0.05 | 0.05 | 0.05 |
| 0.1% | 4788.81 | 1445.91 | 167.09 | 96.43 | 64.83 |
| 0.05% | 5343.62 | 1004.34 | 435.52 | 196.51 | 107.54 |
| Deoxycholate | | | | | |
| 1.0% | 3.98 | 3.63 | 3.63 | 3.15 | 3.24 |
| 0.5% | 3189.56 | 2715.45 | 2268.77 | 2105.38 | 1845.36 |
| 0.1% | 6422.34 | 3730.44 | 1627.81 | 1028.42 | 669.31 |
| 0.05% | 5810.85 | 1729.95 | 738.1 | 375.74 | 188.59 |
| Non-ionic Detergents | | | | | |
| TRITON X-100 | | | | | |
| 1.0% | 6073.78 | 1774.10 | 839.14 | 331.95 | 174.89 |
| 0.5% | 6106.61 | 1880.98 | 871.01 | 378.58 | 195.42 |
| 0.1% | 6837.20 | 3004.57 | 1643.05 | 801.38 | 448.93 |
| 0.05% | 6160.71 | 1964.17 | 822.48 | 303.73 | 147.48 |
| BIGCHAP | | | | | |
| 1.0% | 7576.05 | 4043.35 | 2474.59 | 1374.29 | 822.65 |
| 0.5% | 7438.53 | 3618.22 | 2092.69 | 1144.80 | 677.61 |
| 0.1% | 6607.01 | 2087.01 | 1363.07 | 634.92 | 301.55 |
| 0.05% | 6410.42 | 2260.45 | 1036.69 | 487.72 | 238.44 |
| THESIT ® | | | | | |
| 1.0% | 6204.02 | 1979.43 | 968.14 | 416.45 | 210.78 |
| 0.5% | 6392.75 | 2304.48 | 1122.24 | 487.28 | 240.72 |
| 0.1% | 6022.32 | 2654.97 | 1509.07 | 755.94 | 447.44 |
| 0.05% | 5632.96 | 1601.09 | 623.38 | 211.67 | 110.15 |

TABLE D-continued

| | Average Relative Light Unit Values | | | | |
|---|---|---|---|---|---|
| | 5 min | 75 min | 169 min | 222 min | 260 min |
| Cationic Detergents | | | | | |
| BDDABr | | | | | |
| 1.0% | 0.49 | 0.51 | 0.44 | 0.42 | 0.43 |
| 0.5% | 122.47 | 107.39 | 93.92 | 96.68 | 101.11 |
| 0.1% | 7069.08 | 5136.92 | 3260.59 | 2366.49 | 1767.58 |
| 0.05% | 7077.46 | 4539.97 | 2465.57 | 1680.16 | 1233.82 |
| CTAB | | | | | |
| 1.0% | 0.09 | 0.08 | 0.07 | 0.06 | 0.07 |
| 0.5% | 0.34 | 0.28 | 0.23 | 0.27 | 0.18 |
| 0.1% | 5104.82 | 3607.65 | 1889.29 | 1248.51 | not done |
| 0.05% | 6525.51 | 4029.32 | 2093.80 | 1437.67 | 1002.72 |
| DTAB | | | | | |
| 1.0% | 800.61 | 693.13 | 649.41 | 671.03 | 645.40 |
| 0.5% (day 1) | 5630.61 | 5100.09 | 4957.48 | 4916.46 | 4515.20 |
| 0.5% (day 2) | 6617.08 | 6341.09 | 5977.33 | 5824.18 | 5622.12 |
| 0.1% | 6991.01 | 4753.46 | 2737.36 | 1950.95 | 1408.18 |
| 0.05% | 6487.93 | 3138.81 | 1496.01 | 943.40 | 638.30 |
| Zwitterionic Detergents | | | | | |
| CHAPS | | | | | |
| 1.0% | 7241.33 | 3816.06 | 2348.28 | 1322.30 | 809.22 |
| 0.5% | 7368.91 | 4048.24 | 2548.39 | 1438.57 | 909.15 |
| 0.1% | 6515.77 | 2583.65 | 1236.53 | 448.96 | 284.18 |
| 0.05% | 6356.62 | 2305.56 | 1143.02 | 500.80 | 240.81 |
| CHAPSO | | | | | |
| 1.0% | 7160.63 | 3803.84 | 2376.31 | 1332.97 | 840.57 |
| 0.5% | 7422.26 | 4089.32 | 2581.01 | 1460.54 | 923.81 |
| 0.1% | 6549.85 | 2584.56 | 1210.14 | 558.69 | 280.84 |
| 0.05% | 6396.53 | 2424.54 | 1124.83 | 480.09 | 238.80 |
| Sulfobetaine 3-10 | | | | | |
| 1.0% | 7861.36 | 5703.51 | 4318.46 | 3075.12 | 2193.02 |
| 0.5% | 6565.98 | 2405.95 | 1211.13 | 609.75 | 391.64 |
| 0.1% | 6506.61 | 2367.27 | 1100.37 | 446.29 | 222.22 |
| 0.05% | 6247.31 | 2270.13 | 1053.56 | 465.03 | 233.19 |

TABLE E

| | Percent ATP Remaining | | | | |
|---|---|---|---|---|---|
| Condition | 5 min | 75 min | 169 min | 222 min | 260 min |
| Cell lysate (cationic and anionic) | 100 | 27.5 | 14.2 | 5.7 | 3.0 |
| Cell lysate (nonionic and zwitterionic) | 100 | 34.0 | 18.0 | 7.5 | 3.6 |
| ATP Control (cationic and anionic) | 100 | 83.2 | 87.3 | 100.9 | 78.4 |
| ATP Control (nonionic and zwitterionic) | 100 | 102.5 | 93.6 | 106.2 | 101.0 |
| Anionic Detergents | | | | | |
| SDS | | | | | |
| 0.05% | 100 | 89.7 | 80.4 | 78.0 | 68.0 |
| Bioterge | | | | | |
| 0.1% | 100 | 30.2 | 3.5 | 2.0 | 1.4 |
| 0.05% | 100 | 18.8 | 8.2 | 3.7 | 2.0 |

TABLE E-continued

Percent ATP Remaining

| Condition | 5 min | 75 min | 169 min | 222 min | 260 min |
|---|---|---|---|---|---|
| Deoxycholate | | | | | |
| 0.5% | 100 | 85.1 | 71.1 | 66.0 | 57.9 |
| 0.1% | 100 | 57.9 | 25.3 | 16.0 | 10.4 |
| 0.05% | 100 | 29.8 | 12.7 | 6.5 | 3.2 |
| Non-ionic Detergents | | | | | |
| TRITON X-100 | | | | | |
| 1.0% | 100 | 29.2 | 13.8 | 5.5 | 2.9 |
| 0.5% | 100 | 30.8 | 14.3 | 6.2 | 3.2 |
| 0.1% | 100 | 43.9 | 24.0 | 11.7 | 6.6 |
| 0.05% | 100 | 31.9 | 13.4 | 4.9 | 2.4 |
| BIGCHAP | | | | | |
| 1.0% | 100 | 53.4 | 32.7 | 18.1 | 10.9 |
| 0.5% | 100 | 48.6 | 28.1 | 15.4 | 9.1 |
| 0.1% | 100 | 31.6 | 20.6 | 9.6 | 4.6 |
| 0.05% | 100 | 35.3 | 16.2 | 7.6 | 3.7 |
| THESIT ® | | | | | |
| 1.0% | 100 | 31.9 | 15.6 | 6.7 | 3.4 |
| 0.5% | 100 | 36.0 | 17.6 | 7.6 | 3.8 |
| 0.1% | 100 | 44.1 | 25.1 | 12.6 | 7.4 |
| 0.05% | 100 | 28.4 | 11.1 | 3.8 | 2.0 |
| Cationic Detergents | | | | | |
| BDDABr | | | | | |
| 0.5% | 100 | 87.7 | 76.2 | 78.9 | 82.6 |
| 0.1% | 100 | 72.7 | 46.1 | 33.5 | 25.0 |
| 0.05% | 100 | 64.1 | 34.8 | 23.7 | 17.4 |
| CTAB | | | | | |
| 0.1% | 100 | 70.7 | 37.0 | 24.5 | not done |
| 0.05% | 100 | 61.7 | 32.1 | 22.0 | 15.4 |
| DTAB | | | | | |
| 1.0% | 100 | 86.6 | 81.1 | 83.8 | 80.6 |
| 0.5% (1) | 100 | 90.6 | 88.0 | 87.3 | 80.2 |
| 0.5% (2) | 100 | 95.8 | 90.3 | 88.0 | 85.0 |
| 0.1% | 100 | 68.0 | 39.2 | 27.9 | 20.1 |
| 0.05% | 100 | 48.4 | 23.1 | 14.5 | 9.8 |
| Zwitterionic Detergents | | | | | |
| CHAPS | | | | | |
| 1.0% | 100 | 52.7 | 32.4 | 18.3 | 11.2 |
| 0.5% | 100 | 54.9 | 34.6 | 19.5 | 12.3 |
| 0.1% | 100 | 39.7 | 19.0 | 8.6 | 4.4 |
| 0.05% | 100 | 36.3 | 18.0 | 7.9 | 3.8 |
| CHAPSO | | | | | |
| 1.0% | 100 | 53.1 | 33.2 | 18.6 | 11.7 |
| 0.5% | 100 | 55.1 | 34.8 | 19.7 | 12.4 |
| 0.1% | 100 | 39.5 | 18.5 | 8.5 | 4.3 |
| 0.05% | 100 | 37.9 | 17.6 | 7.5 | 3.7 |
| Sulfobetaine 3-10 | | | | | |
| 1.0% | 100 | 72.6 | 54.9 | 39.1 | 27.9 |
| 0.5% | 100 | 36.6 | 18.4 | 9.3 | 6.0 |
| 0.1% | 100 | 36.4 | 16.9 | 6.9 | 3.4 |
| 0.05% | 100 | 36.3 | 16.9 | 7.4 | 3.7 |

The data demonstrate that for the anionic detergents tested, SDS at concentration 0.05% and deoxycholate at concentrations 0.5% and 0.1% slow the degradation of endogenous ATP in the cell lysate resulting in from about three to about twenty times more ATP present in the sample after four hours when the detergent was present than when it was absent indicating inhibition of ATPase endogenous to the sample. The non-ionic detergents had little, if any, additional ATP present in the sample after four hours in the presence of the detergent than in the absence of the detergent indicating that these detergents did not inhibit endogenous ATPase. The zwitterionic detergents tested had three to four times more ATP present in the sample after four hours when the detergent was present than when it was absent. The most significant results were seen when cationic detergents were incubated with the cell lysate. BDDABr at 0.5% concentration, and DTAB at 0.5% and 1.0% concentrations, each had at least 25-fold more ATP present in the sample after four hours than samples without these detergents. CTAB at 0.05% concentration had about four times more ATP present in the sample after four hours when the detergent was present than when it was absent.

Example 2

II. Detergents That Inhibit ATPases

This example tested the seven detergents that demonstrated inhibition of ATPase activity in Example 1 herein above at a lower percentage than was previously tested. The experiment was performed as detailed in Example 1. The average relative light unit values and the percent of ATP remaining values are listed below in Table F and G respectively.

TABLE F

Average Relative Light Unit Values

| | 5 min | 75 min | 169 min | 222 min | 260 min |
|---|---|---|---|---|---|
| Controls | | | | | |
| Cell Lysate | 5296.25 | 1613.68 | 334.28 | 225.95 | 123.08 |
| ATP + Hepes | 22565.95 | 16238.00 | 20241.55 | 19302.50 | 18528.1 |
| Samples | | | | | |
| 0.5% DTAB | 5189.8 | 4564.65 | 4111.89 | 4230.51 | 4267.32 |
| 0.02% DTAB | 5870.43 | 1997.09 | 435.05 | 329.83 | 227.72 |
| 0.02% BDDABr | 6215.32 | 2686.49 | 962.85 | 604.47 | 429.86 |
| 0.02% Sulfobetaine | 6120.5 | 1622.61 | 291.09 | 245.55 | 136.43 |
| 0.02% Deoxycholate | 5962.61 | 1694.47 | 368.11 | 241.05 | 135.25 |
| 0.01% SDS | 13116.20 | 10753.03 | 12051.63 | 11822.03 | 11900.73 |
| 0.002% SDS | 5773.39 | 1574.34 | 278.67 | 236.28 | 128.58 |

TABLE G

Percent ATP Remaining

| Condition | 5 min | 75 min | 169 min | 222 min | 260 min |
|---|---|---|---|---|---|
| Lysate Control | 100.00 | 30.47 | 6.31 | 4.27 | 2.32 |
| ATP Control | 100.00 | 71.96 | 89.70 | 85.54 | 82.11 |
| 0.5% DTAB | 100.00 | 87.95 | 79.23 | 81.52 | 82.23 |
| 0.02% DTAB | 100.00 | 34.02 | 7.41 | 5.62 | 3.88 |
| 0.02% CTAB | 100.00 | 43.22 | 15.49 | 9.73 | 6.92 |
| 0.02% BDDABr | 100.00 | 48.53 | 21.51 | 13.18 | 9.74 |
| 0.02% Sulfobetaine | 100.00 | 26.51 | 4.76 | 4.01 | 2.23 |
| 0.02% Deoxychol. | 100.00 | 28.42 | 6.17 | 4.04 | 2.27 |
| 0.01% SDS | 100.00 | 48.62 | 25.80 | 14.20 | 8.79 |
| 0.002% SDS | 100.00 | 27.27 | 4.83 | 4.09 | 2.23 |

The log of the percent of ATP remaining after original timepoint values from Table E and Table G were plotted on the y axis against time (in minutes) on the x axis. The slope of the line generated by these values in the presence of detergent was divided by the slope of the line generated by the values in the absence of detergent (lysate control) resulting in the Relative ATPase Activity values listed below in Table H.

TABLE H

RELATIVE ATPase ACTIVITY

Relative ATPase Activity

| | Percent detergent | Slope | slope det/slope lysate |
|---|---|---|---|
| Controls: | | | |
| Cell lysate (cat & an) | | −0.0056 | 1.000 |
| Cell lysate (zwit & non) | | −0.0053 | 1.000 |
| ATP control (cat & an) | | −0.0002 | 0.030 |
| ATP control (zwit & non) | | 0.00002 | −0.005 |
| ATP control for detergents less than 0.05% | | −0.00013 | 0.02 |
| Anionic: | | | |
| SDS | 1.00 | — | — |
| | 0.50 | — | — |
| | 0.10 | — | — |
| | 0.05 | −0.0006 | 0.105 |
| | 0.01 | −0.00385 | 0.702 |
| | 0.002 | −0.0064 | 1.010 |
| Bioterge | 1.00 | — | — |
| | 0.50 | — | — |
| | 0.10 | −0.0076 | 1.366 |
| | 0.05 | −0.0062 | 1.113 |
| Deoxycholate | 1.00 | — | — |
| | 0.50 | −0.0009 | 0.158 |
| | 0.10 | −0.0038 | 0.684 |
| | 0.05 | −0.0055 | 0.984 |
| | 0.02 | −0.0064 | 1.004 |
| Non-ionic: | | | |
| Triton X-100 | 1.00 | −0.0061 | 1.152 |
| | 0.50 | −0.0059 | 1.117 |
| | 0.10 | −0.0047 | 0.889 |
| | 0.05 | −0.0065 | 1.228 |
| BIGCHAP | 1.00 | −0.0038 | 0.725 |
| | 0.50 | −0.0041 | 0.782 |
| | 0.10 | −0.0051 | 0.968 |
| | 0.05 | −0.0056 | 1.069 |
| THESIT ® | 1.00 | −0.0058 | 1.096 |
| | 0.50 | −0.0056 | 1.065 |
| | 0.10 | −0.0045 | 0.850 |
| | 0.05 | −0.0068 | 1.295 |
| Cationic: | | | |
| BDDABr | 1.00 | — | — |
| | 0.50 | −0.0004 | 0.064 |
| | 0.10 | −0.0023 | 0.414 |
| | 0.05 | −0.0030 | 0.528 |
| | 0.02 | −0.0039 | 0.623 |
| CTAB | 1.00 | — | — |
| | 0.50 | — | — |
| | 0.10 | −0.0028 | 0.507 |
| | 0.05 | −0.0031 | 0.561 |
| | 0.02 | −0.0046 | 0.718 |
| DTAB | 1.00 | −0.0003 | 0.057 |
| | 0.50 | −0.0003 | 0.055 |
| | 0.50 | −0.0003 | 0.048 |
| | 0.10 | −0.0027 | 0.480 |
| | 0.05 | −0.0039 | 0.690 |
| | 0.02 | −0.0056 | 0.884 |

TABLE H-continued

RELATIVE ATPase ACTIVITY

Relative ATPase Activity

| | Percent detergent | Slope | slope det/slope lysate |
|---|---|---|---|
| Zwitterionic: | | | |
| CHAPS | 1.00 | −0.0038 | 0.715 |
| | 0.50 | −0.0036 | 0.688 |
| | 0.10 | −0.0054 | 1.023 |
| | 0.05 | −0.0056 | 1.061 |
| CHAPSO | 1.00 | −0.0037 | 0.703 |
| | 0.50 | −0.0036 | 0.685 |
| | 0.10 | −0.0054 | 1.030 |
| | 0.05 | −0.0057 | 1.080 |
| Sulfobetaine 3-10 | 1.00 | −0.0022 | 0.417 |
| | 0.50 | −0.0049 | 0.921 |
| | 0.10 | −0.0058 | 1.109 |
| | 0.05 | −0.0057 | 1.077 |
| | 0.02 | −0.0064 | 1.009 |

A relative activity value of 1.0 or greater indicates 100% cellular ATPase activity at the concentration of detergent tested. A relative activity value of 0.5 indicates a two-fold (or 50%) decrease in the level of cellular ATPase activity at the concentration of detergent tested when compared to the ATPase activity level in the absence of the detergent. A relative activity value of 0.2 indicates a five-fold (or 80%) decrease in the level of cellular ATPase activity at the concentration of detergent tested when compared to the ATPase activity level in the absence of the detergent.

For the cationic detergents tested, the reaction conditions which resulted in a 25% or greater decrease in the relative ATPase activity were DTAB at concentrations of 0.05% and greater; CTAB at concentrations of 0.02% and greater; BDDABr at concentrations of 0.02% and greater. Therefore, all cationic detergents tested in this assay at a concentration of 0.05% or greater decreased cellular ATPase activity by 25% or more. For the anionic detergents tested, the reaction conditions which resulted in a 25% or greater decrease in relative ATPase activity compared to reactions in the absence of detergent were SDS at concentrations of 0.01% and greater and deoxycholate at concentrations of 0.1% and greater. None of the nonionic detergents tested resulted in a 25% or greater decrease in the level of cellular ATPase activity. For the zwitterionic detergents tested, only sulfobetaine at a concentration of 1% or greater was able to decrease the relative ATPase activity by 25% or greater compared to reactions in the absence of detergent.

Figure 2:
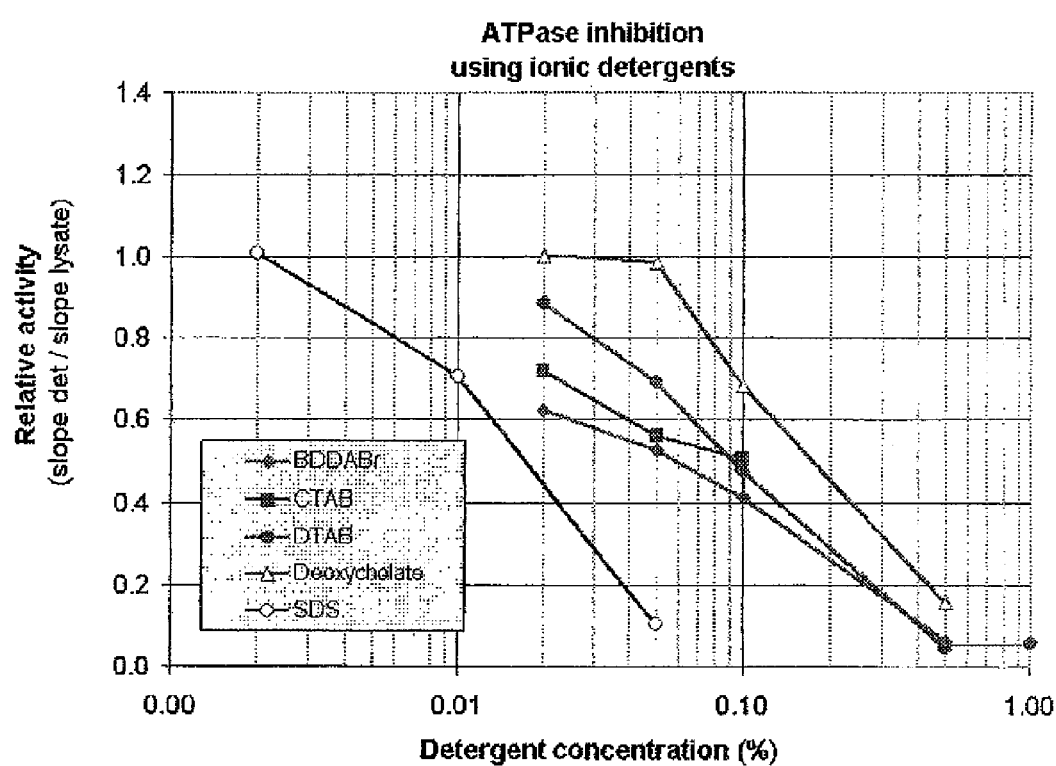
FIG. 2 is a graph illustrating the effect of increasing concentrations of various cationic or anionic detergents on relative ATPase activity in a sample.

These values are graphed in FIG. 1 (nonionic and zwitterionic detergents) and FIG. 2 (cationic and anionic detergents).

Example 3

Stability of Reagent Composition (Room Temp.)

The detergents used for inhibition of endogenous ATPase activity in a sample also affect activity of luciferase. This example was designed to test the stability and functionality of the reagent composition ("reagent composition") over time when it comprised different luciferase enzymes and when the ATPase inhibitor was present at a concentration that significantly inhibited the ATPase activity endogenous to the sample as demonstrated in Example 1 and Example 2 herein above. It is ultimately the extended stability of a reagent composition, comprising an ATPase inhibitor and a luciferase enzyme, which provides a composition useful for measuring ATP, in a sample or samples, over an extended period of time. The most preferred luciferase for use in such a reagent composition would be one whose stability is minimally decreased in the presence of an ATPase inhibitor when that ATPase inhibitor is present in the reagent composition at a concentration capable of inhibiting at least 30% ATPase activity endogenous to the sample.

In this experiment, the stability of a reagent composition comprising wild type LucPpy was compared to the stability of a reagent composition comprising LucPpe2m146 at about 23° C. (room temperature). The various reagent compositions had varying detergent concentrations. The various detergents tested were those demonstrated in Examples 1 and 2 above to have significant ATPase inhibition activity.

Two solutions were created as listed below. One contained the luciferase, luciferin, $MgSO_4$, and buffer (reagent composition). The other solution contained media plus ATP (media solution).

Reagent Composition:
    50 μg/ml enzyme (LucPpy is Promega catalog #E170A)
    50 mM Hepes buffer (pH 7.0)
    100 mM NaCl
    1.0 mM EDTA
    0.1% gelatin
    10 mM $MgSO_4$
    1.0 mM Luciferin
    Detergent (at various concentrations, see table below)
    Nanopure water was added to a final volume of 2.5 ml Media Solution:
    F12/DME media (Sigma D-6905) final volume 15 ml
    1.0 μM ATP For each reagent composition, all ingredients except the luciferase enzyme were assembled; the enzyme was then added immediately before the first luminescence reading was taken. Immediately after addition of enzyme to each reagent composition and for various timepoints thereafter, 100 μl aliquots of the reagent composition were added to wells of a 96-well microtitre luminometer plate in triplicate. To these were added 100 μl Media Solution containing the ATP. Luminescence was then immediately read on a Dynex MLX microtitreplate luminometer, 0.5 second reads per well. The average relative light unit values as well as the reaction half lives are listed below in Table I and the percent of original luminescence remaining at each timepoint is listed in Table J below. The timepoint at the top of the column indicates the time at which the first RLU measurement for the samples in that column was read. Times are provided for some samples when their time of measurement varied significantly from the time at the top of the column. Times listed in Table I are the same for Table J. The values for sulfobetaine and for CTAB were generated on different days, they are presented with the control values generated in the same experiment. There was substantial precipitation in the samples containing 0.5% deoxycholate and slight precipitation in the samples containing 0.1% deoxycholate. This resulted in unreliable measurements for those samples.

TABLE I

Average Relative Light Units

LucPpy (at RT, pH 7.0)

|  | 0.75 min | 21 min | 39 min | 64 min | 92 min |
|---|---|---|---|---|---|
| Control (no det) | 3620.263 | 3610.837 | 3530.333 | 3421.743 | 3442.863 |
| DTAB 0.5% | 0.018 | | | | |
| BDDABr 0.5% | 0.001 | | | | |
| *Deoxych. 0.5% | 4.801 | 0.012 | 0.007 | | |
| SDS 0.05% | 0.007 | | | | |

|  | 0.75 min | 7.5 min | 20.5 min | 59 min | 90 min |
|---|---|---|---|---|---|
| Control (no det) | 3238.01 | 3147.54 | 3192.85 | 3155.05 | 3203.21 |
| Sulfobet. 1.0% | 0.024 | 0.000 | | | |
| Sulfobet. 0.5% | 737.788 | 0.084 | 0.037 | | |
| Sulfobet. 0.1% | 3291.41 | 3178.07 | 3262.17 | 3074.49 | 3066.29 |

|  | 0.75 min | 10 min | 36 min | 60 min | 95 min |
|---|---|---|---|---|---|
| Control (no det) | 2311.293 | — | 2294.607 | 2254.490 | 2196.130 |
| DTAB 0.1% | 0.307 | 0.009 | 0.005 | | |
| BDDABr 0.1% | 0.007 | | | | |
| SDS 0.01% | 0.175 | 0.016 | | | |
| *Deoxych. 0.1% | 19.771 | 0.180 | 0.026 | | |

|  | 0.75 min | 6 min | 20 min | 40 min | 62 min | 88 min |
|---|---|---|---|---|---|---|
| Control (no det) | 2844.21 | — | 2672.94 | 2817.67 | 2869.35 | 2852.75 |
| *CTAB 0.1% | 94.603 | 0.020 | | | | |
| *CTAB 0.05% | 1134.53 | 0.563 | 0.015 | | | |
| *CTAB 0.02% | 1869.80 | 79.719 | 0.099 (16 min) | | | |

|  | 0.75 min | 38 min | 70 min | 94 min | 122 min |
|---|---|---|---|---|---|
| Control (no det) | 3379.970 | 3194.540 | 3085.880 | 3015.030 | 2820.330 |
| DTAB 0.02% | 4513.320 | 3761.940 | 3363.410 | 3229.340 | 3082.030 |
| BDDABr 0.02% | 2894.700 | 0.035 | 0.015 | 0.016 | 0.011 |

TABLE I-continued

| Average Relative Light Units | | | | | |
|---|---|---|---|---|---|
| Deoxych 0.02% | 3199.250 | 2844.010 | 2626.260 | 2496.570 | 2314.910 |
| SDS 0.01% | 17.584 | 0.001 | | | |
| SDS 0.002% | 640.290 | 190.860 | 84.210 | 47.210 | 25.630 |

| LucPpe2m146 (at RT, pH 7.0) | | | | | |
|---|---|---|---|---|---|
| | 15 min | 72 min | 124 min | 190 min | 251 min |
| Control (no det) | 27668.0 | 25171.53 | 24023.967 | 23200.600 | 20771.450 |
| DTAB 0.5% | 5.496 | 3.141 | 2.769 | 2.563 | 2.766 |
| BDDABr 0.5% | 2.040 | 1.140 | 0.998 | 0.899 | 1.042 |
| *Deoxych. 0.5% | 45.977 | 229.874 | 2059.397 | 1414.397 | 1342.963 |
| SDS 0.05% | 0.018 | 0.012 | 0.001 | 0.006 | 0.016 |

| | 0.75 min | 30 min | 66 min | 123 min | 180 min | 238 min |
|---|---|---|---|---|---|---|
| Control (no det) | 16897.5 | 16754.97 | 17594.7 | 16842.8 | 16935.5 | 17598.6 |
| Sulfobet. 1.0% | 16897.5 | 16754.97 | 7036.0 | 6653.67 | 7358.44 | 6948.05 |
| Sulfobet. 0.5% | 13447.0 | 13597.97 | 14186.93 | 12982.20 | 14348.90 | 13958.2 |
| Sulfobet. 0.1% | 16648.3 | 17003.0 | 17849.8 | 16610.13 | 17115.63 | 18131.37 |

| | 1.0 min | 34 min | 65 min | 115 min | 175 min | 238 min | 286 min |
|---|---|---|---|---|---|---|---|
| Control (no det) | 27811.33 | 28665.87 | 28814.47 | 26614.43 | 27752.97 | 28249.6 | 27110.13 |
| DTAB 0.1% | 20132.47 | 20574.63 | 20800.80 | 19908.30 | 20760.93 | 19758.4 | 19659.10 |
| BDDABr 0.1% | 29.71 | 66.09 | 62.19 | 45.18 | 33.89 | 34.46 | 126.90 |
| *Deoxych. 0.1% | 5150.43 | 5031.12 | 6855.67 | 6340.45 | 7347.09 | 6801.23 | 7472.54 |
| SDS 0.01% | 24.46 | 27.85 | 10.77 | 6.45 | 2.02 | 2.44 | 0.62 |

| | 1.0 min | 37 min | 67 min | 116 min | 177 min | 243 min |
|---|---|---|---|---|---|---|
| Control (no det) | 16578.6 | 15270.1 | 15710.6 | 16272.3 | 17085.8 | 17163.7 |
| *CTAB 0.1% | 1047.8 | 5.3 | 5.2 | 6.2 | 6.0 | 5.7 |
| *CTAB 0.05% | 11992.5 | 301.5 | 131.7 | 4219.7 | 16910.8 | 17340.0 |
| *CTAB 0.02% | 11019.8 | 2051.7 | 1087.4 | 6117.8 | 16020.8 | 16368.5 |

| | 1.0 min | 34 min | 65 min | 115 min | 175 min | 238 min | 286 min |
|---|---|---|---|---|---|---|---|
| Control (no det) | 27811.33 | 28665.87 | 28814.47 | 26614.43 | 27752.97 | 28249.6 | 27110.1 |
| DTAB 0.02% | 28730.17 | 28596.30 | 28651.97 | 26062.30 | 27941.73 | 27677.9 | 27808.3 |
| BDDABr 0.02% | 26548.60 | 26272.87 | 25766.43 | 24155.00 | 25891.70 | 24959.1 | 24510.1 |
| Deoxych. 0.02% | 24307.30 | 24639.00 | 24717.97 | 23158.37 | 24655.43 | 24320.6 | 24303.9 |
| SDS 0.002% | 24265.83 | 24213.97 | 24725.73 | 22654.87 | 23856.73 | 23425.5 | 23275.6 |

*ppt indicates that the detergent precipitated in the sample

For each concentration of detergent using either luciferase, the stability of the reagent composition can be described as having an activity half-life using the data from Table J. The half-life is determined by applying linear regression to the data, with the logarithm of the relative luminescence values in Table J as the dependent variable, and the time of each measurement as the independent variable. The half-life is then calculated from the linear regression as ln(0.5)/(slope). Using this method, the stabilities of the reagent composition are listed in Table K; detergent concentration shown as percent (w/v) and values of activity half-life shown in minutes. Where the luminescence activity was less than could be reliably measured, the half-life is shown as "no activity." Some reagent compositions were very unstable, having activity half-lives less than 10 minutes. Because these are difficult to accurately quantitate, they are listed only as "<10." In contrast, some reagent compositions exhibited large stability, having activity half-lives greater than 1000 minutes (i.e., greater than 16 hours). Because the samples were measured for fewer than 5 hours, accurate determinations of half-lives are difficult and are listed only as ">1000."

TABLE J

| Percent of Luminescence Remaining | | | | | |
|---|---|---|---|---|---|
| LucPpy (at RT, pH 7.0) | | | | | |
| Control (no det) | 100.00 | 99.74 | 97.52 | 94.52 | 95.10 |
| DTAB 0.5% | 100.00 | | | | |
| BDDABr 0.5% | 100.00 | | | | |

TABLE J-continued

Percent of Luminescence Remaining

| | | | | | | |
|---|---|---|---|---|---|---|
| Deoxych. 0.5% | 100.00 | 0.25 | 0.15 | | | (ppt) |
| SDS 0.05% | 100.00 | | | | | |
| Control (no det) | 100.00 | 97.2 | 98.6 | 108.5 | 97.4 | 98.9 |
| Sulfobet. 0.5% | 100.00 | | | | | |
| Sulfobet. 0.1% | 100.00 | 95.8 | 99.1 | 93.4 | 93.2 | |
| Control (no det) | 100.00 | nd | 99.28 | 97.54 | 95.02 | |
| DTAB 0.1% | 100.00 | 2.93 | 1.55 | | | |
| BDDABr 0.1% | 100.00 | | | | | |
| SDS 0.01% | 100.00 | 9.14 | | | | |
| Deoxychol 0.1% | 100.00 | 0.91 | 0.13 | | | |
| Control (no det) | 100.00 | — | 94.0 | 99.1 | 100.9 | |
| CTAB 0.1% | 100.00 | 0.02 | | | | Ppt. |
| CTAB 0.05% | 100.00 | 0.05 | 0.00 | | | Ppt. |
| CTAB 0.02% | 100.00 | 0.09 | 0.03 | | | Ppt. |
| Control (no det) | 100.00 | 94.51 | 91.30 | 89.20 | 83.44 | |
| DTAB 0.02% | 100.00 | 99.53 | 74.52 | 71.55 | 68.29 | |
| BDDABr 0.02% | 100.00 | 0.00 | 0.00 | | | |
| Deoxych. 0.02% | 100.00 | 88.90 | 82.09 | 78.04 | 72.36 | |
| SDS 0.002% | 100.00 | 29.81 | 13.15 | 7.37 | 4.00 | |

LucPpe2m146 (at RT, pH 7.0)

| | | | | | | | |
|---|---|---|---|---|---|---|---|
| Control (no det) | 100.00 | 90.98 | 86.83 | 83.85 | 75.07 | | |
| DTAB 0.5% | 100.00 | 57.16 | 50.39 | 46.64 | 50.32 | | |
| BDDABr 0.5% | 100.00 | 55.90 | 48.93 | 44.07 | 51.10 | | |
| Deoxychol 0.5% | 100.00 | 499.98 | 4479.22 | 3076.34 | 2920.97 | Substantial precipitation | |
| SDS 0.05% | 100.00 | 65.68 | 6.09 | 35.06 | 87.64 | | |
| Control (no det) | 100.0 | 99.2 | 104.1 | 99.7 | 100.2 | 104.1 | |
| Sulfobet. 1.0% | 100.00 | 102.0 | 106.0 | 100.3 | 110.9 | 104.7 | |
| Sulfobet. 0.5% | 100.00 | 101.1 | 105.5 | 96.5 | 106.7 | 103.8 | |
| Sulfobet. 0.1% | 100.00 | 102.1 | 107.2 | 99.8 | 102.8 | 108.9 | |
| Control (no det) | 100.00 | 103.07 | 103.61 | 95.70 | 99.79 | 101.58 | 97.48 |
| DTAB 0.1% | 100.00 | 102.20 | 103.32 | 98.89 | 103.12 | 98.1 | 97.65 |
| BDDABr 0.1% | 100.00 | 222.47 | 209.32 | 152.09 | 114.06 | 115.98 | 427.13 |
| Deoxychol 0.1% | 100.00 | 97.68 | 133.11 | 123.11 | 142.65 | 132.05 | 145.09 Precip. |
| SDS 0.01% | 100.00 | 113.85 | 44.02 | 26.38 | 8.25 | 9.97 | 2.53 |
| Control (no det) | 100.00 | 92.11 | 94.76 | 98.15 | 103.06 | 103.53 | |
| CTAB 0.1% | 100.00 | 0.51 | 0.50 | 0.59 | 0.58 | 0.55 | Ppt |
| CTAB 0.05% | 100.00 | 2.51 | 1.10 | 35.19 | 141.01 | 144.59 | Ppt |
| CTAB 0.02% | 100.00 | 18.62 | 9.87 | 55.52 | 145.38 | 148.54 | Ppt |
| Control (no det) | 100.00 | 103.07 | 103.61 | 95.70 | 99.79 | 101.58 | 97.48 |
| DTAB 0.02% | 100.00 | 99.53 | 99.73 | 90.71 | 97.26 | 96.34 | 96.79 |
| BDDABr 0.02% | 100.00 | 98.96 | 97.05 | 90.98 | 97.53 | 94.01 | 92.32 |
| Deoxych. 0.02% | 100.00 | 101.36 | 101.69 | 95.27 | 101.43 | 100.05 | 99.99 |
| SDS 0.002% | 100.00 | 99.79 | 101.90 | 93.36 | 98.31 | 96.54 | 95.92 |

In Table K, the values below the horizontal line (in bold) indicate the concentrations of each detergent that inhibited endogenous ATPase activity in Examples 1 and 2 by at least 25%. It is clear that the reagent composition is very unstable when comprising LucPpy and has a concentration of detergent capable of inhibiting at least 25% of the endogenous ATPase activity. In contrast, a reagent comprising LucPpe2 ml 46 and the same detergent concentration generally has moderate to substantial stability. In some cases, luciferase activity was inhibited by the presence of the detergent, but nonetheless yielded a stable composition. Two detergents, CTAB and deoxycholate, precipitated from the solution during the course of the measurements. This was most notable for CTAB, where LucPpe2ml 46 was strongly inactivated by the detergent, but slowly regained activity as the detergent precipitated from solution. This behavior made half-life impossible to estimate for the reagent composition containing CTAB. The effect was seen to a lesser extent with deoxycholate.

TABLE K

Half-life of Luminescence Activity (measured in minutes)

| conc. | DTAB | CTAB | BDDABr | Deoxych. | SDS | Sulfobetaine |
|---|---|---|---|---|---|---|
| | | | Common firefly luciferase (P. pyralis) | | | |
| 0.000 | >1000 | >1000 | >1000 | >1000 | >1000 | >1000 |
| 0.002 | | | | | 25 | |
| 0.010 | | | | | <10 | |
| 0.020 | 193 | <10* | <10 | 235 | | |
| 0.050 | | <10* | | | no activity | |
| 0.100 | <10 | <10* | no activity | <10* | | 877 |
| 0.200 | | | | | | |
| 0.500 | no activity | | no activity | <10* | | no activity |
| 1.000 | | | | | | |

TABLE K-continued

Half-life of Luminescence Activity (measured in minutes)

| conc. | DTAB | CTAB | BDDABr | Deoxych. | SDS | Sulfobetaine |
|---|---|---|---|---|---|---|
| | | | Chemostable luciferase (Ppe2m146) | | | |
| 0.000 | >1000 | | >1000 | >1000 | >1000 | >1000 |
| 0.002 | | | | | >1000 | |
| 0.010 | | | | | 83 | |
| 0.020 | >1000 | * | >1000 | >1000 | | |
| 0.050 | | * | | | | |
| 0.100 | >1000 | * | >1000 | >1000* | | >1000 |
| 0.200 | | | | | | |
| 0.500 | 265 | | 264 | >1000* | | >1000 |
| 1.000 | | | | | | >1000 |

*precipitate formed

Example 4

ATPase Inhibition at 22° C. and 37° C.

Cell lysate was prepared as described in Example 1. The ability of 1% DTAB to inhibit endogenous ATPase (i.e., ATPase present in a sample) was measured in a complete reagent composition over time at both 22° C. (room temperature) and 37° C. Three cell lysate samples were prepared. Sample 1 contained 4.0 ml L929 cell lysate plus 4.0 ml 25 mM Hepes, pH 7.5. Sample 2 contained 4.0 ml L929 cell lysate plus 4.0 ml buffered detergent solution (40 mM Citrate (pH 6.0), 110 mM MES (pH 6.0), 450 mM KPO4 (pH 6.0), 2.0 mM EDTA, 0.2% Mazu DF-204 (PPG Industries), 2.0 mM NaF, 1.0% DTAB and 2% THESIT®—final pH of the buffered detergent solution adjusted to 6.0). Sample 3 contained 4.0 ml DMEM/F12 media (no serum) containing 0.1 µM ATP plus 4.0 ml 25 mM Hepes (pH 7.5). The samples were divided in half—half was incubated at 22° C.; half was incubated at 37° C. After 10 minutes of incubation in their respective water baths to allow the solution at 37° C. to reach that temperature (this point is referred to as time=10 min.), 100 µl of each sample was transferred independently to a well of a 96-well luminometer plate in quadruplicate. To each 100 µl sample was added 20 µl of a solution containing luciferin (12.5 mM/luciferase (200 µg/ml LucPpe2m146)/MgSO4 (50 mM solution. The resulting relative light units were measured on a Dynex luminometer using 0.5 second reads. This was repeated at several time points out to five hours. The resulting average relative light unit values (Table L) and the percent remaining ATP (Table M) are below.

TABLE L

Average Relative Light Unit Values

| | Time (minutes) | | | | | |
|---|---|---|---|---|---|---|
| Temp. | 10 min | 60 min | 110 min | 180 min | 240 min | 300 min |
| 37° C. | | | | | | |
| Sample 1 | 12371.2 | 3141.2 | 930.0 | 270.7 | 127.4 | 55.1 |
| Sample 2 | 781.3 | 792.3 | 777.5 | 748.9 | 728.2 | 713.4 |
| Sample 3 | 2937.2 | 2815.0 | 2869.2 | 2592.3 | 2046 | 1953.4 |
| 22° C. | | | | | | |
| Sample 1 | 13073.4 | 5551.8 | 2766.29 | 1121.5 | 541.8 | 273.7 |
| Sample 2 | 606.6 | 615.5 | 630.0 | 615.7 | 616.4 | 626.0 |
| Sample 3 | 2603.4 | 2527.0 | 2533.0 | 2321.9 | 2052.8 | 1917.3 |

TABLE M

Percent ATP Remaining

| | Relative light units | | | | | |
|---|---|---|---|---|---|---|
| Temp | 10 min | 60 min | 110 min | 180 min | 240 min | 300 min |
| 37° C. | | | | | | |
| Sample 1 | 100 | 25.39 | 7.52 | 2.19 | 1.03 | 0.44 |
| Sample 2 | 100 | 101.41 | 99.51 | 95.86 | 93.20 | 91.31 |
| Sample 3 | 100 | 95.84 | 97.69 | 88.26 | 69.68 | 66.51 |
| 22° C. | | | | | | |
| Sample 1 | 100 | 42.47 | 21.16 | 8.58 | 4.14 | 2.09 |
| Sample 2 | 100 | 101.46 | 103.86 | 101.5 | 101.62 | 103.21 |
| Sample 3 | 100 | 97.07 | 97.30 | 89.19 | 78.85 | 73.65 |

Under the conditions of this assay, 1% DTAB resulted in no loss of ATP (i.e., complete inhibition of ATPase endogenous to the sample) at 22° C. and minimal loss at 37° C., even when the solution was incubated at the temperature of interest for up to five hours. These data demonstrate reaction conditions for which there is nearly complete endogenous ATPase inhibition, yet in which ATP is stable to at least five hours.

Example 5

III. Stability of Reagent Composition

Using the results of Example 4, this experiment was designed to demonstrate the stability of the complete reagent composition at 22° C. in comparison to its stability at 37° C. as measured by luminescence over time. To generate the complete reagent composition, 10 ml of buffered detergent (36 mM Sodium Citrate, 2 mM EDTA, 20 mM MgSO4, 2 mM NaF, 1% DTAB, 2% THESIT®, 0.2% Mazu, buffered to a final pH of 6.0) was added to lyophilized LucPpe2m146, D-luciferin, MgSO4, CDTA so that the reagent composition had a final luciferase concentration of 80 µg/ml and final luciferin concentration of 5 mM.

The reagent composition was divided in half with one half incubated at 22° C. and the other half incubated in a water bath at 37° C. At various timepoints, 100 µl samples were removed from the reagent compositions (in quadruplicate) and transferred to a 96 well luminometer plate. Then, to each 100 µl sample was added 100 µl of 1.0 µM ATP in DPBS (Dulbecco's Phosphate Buffered Saline, Sigma Corp., St. Louis, Mo.). The plate was shaken for 30 seconds at 700 rpm on an orbital shaker and luminescence was then read on a Dynex MLX microtiter plate luminometer, 0.5 second reads per well. The average relative light unit values are listed below in Table N and the percent remaining ATP and half life values in Table O.

TABLE N

Average Relative Light Units

| | Time (min.): | | | | | | |
|---|---|---|---|---|---|---|---|
| | 0 | 23 | 60 | 120 | 185 | 240 | 300 |
| 22° C. | 695.4 | 763.0 | 741.8 | 683.8 | 675.9 | 664.4 | 681.4 |
| 37° C. | — | 757.7 | 722.3 | 614.4 | 575.0 | 544.2 | 526.1 |

TABLE O

Percent Remaining ATP

| | Time (min.): | | | | | | | |
|---|---|---|---|---|---|---|---|---|
| | 0 | 23 | 60 | 120 | 185 | 240 | 300 | half-life |
| 22° C. | 100 | 109.7 | 106.7 | 98.3 | 97.2 | 95.5 | 98.0 | >1000 min |
| 37° C. | 100 | 108.9 | 103.9 | 88.4 | 82.7 | 78.2 | 75.7 | 573 min |

Example 6

DTAB Effect on Stability of Reagent Compositions Comprising Various Luciferases (37° C.)

The stability of a reagent composition comprising LuePpe2 luciferase was compared to a reagent composition comprising LucPpe2m90 and a reagent composition comprising LucPpe2m146, in the presence and absence of 0.1% DTAB. These mutant luciferases are thermostable; they are described in detail in PCT application PCT/US99/30925, filed Dec. 22, 1999.

Each enzyme was diluted to 0.05 mg/ml to a final volume of 1.0 ml in either 25 mM HEPES, pH 8.0 or 20 mM citrate, pH 6.0; both with 100 mM NaCl, 1 mM EDTA, 0.1% gelatin and 5% glycerol. In half of the samples, 0.1% DTAB was added. The enzyme solutions ("reagent compositions") were incubated at 37° C.

At various timepoints, 10 µl of enzyme solution was transferred to a 96-well luminometer plate in triplicate. Then, in triplicate, 100 µl room temperature luciferase assay reagent (1 mM luciferin, 0.2 mM ATP, 10 mM MgSO$_4$ in 50 mM HEPES, pH 8.0) was added to each 10 µl enzyme solution aliquot, mixed and immediately read in a Dynex MLX microtiter plate luminometer. The ATP in the luciferase assay reagent is at a saturated concentration. The average RLU values are reported, as are the half lives of the reagent composition activity as measured by luminescence (Table P). Half-life was calculated using the formula log (0.5)/slope of the data plotted as time (x axis) versus log value of RLU. The time 0 is actually about 2-3 minutes after the mixing of enzyme and substrate; this could account for the lower numbers in the presence of DTAB at time 0 than in the absence of DTAB.

TABLE P

Effect of DTAB on various luciferases' activity

| | Average RLU over time (min) | | | |
|---|---|---|---|---|
| Enzyme/time (min) | pH 6.0 | pH 6.0 + DTAB | pH 8.0 | pH 8.0 + DTAB |
| | LucPpe2 | | | |
| 0 | 18655.25 | 2372.31 | 22134.0 | 7048.95 |
| 29 | 1854.83 | 0.099 | 11773.67 | 0.161 |
| 59 | 206.69 | 0.08 | 5070.62 | 0.034 |
| Half life (min) | 9.1 | 4.0 | 27.7 | 3.4 |
| | LucPpe2m90 | | | |
| 0 | 20031.03 | 16263.53 | 15795.17 | 22401.4 |
| 59 | 18453 | 15535.4 | 15510.77 | 15332.67 |
| 123 | 15966.03 | 13421.5 | 13735.67 | 12383.75 |
| 183 | 15546.4 | 14061.8 | 13271.05 | 11271.25 |
| 239 | 14519.63 | 11924.03 | 11115.13 | 9551.65 |
| Half life (min) | 510.5 | 580.1 | 487.5 | 207.1 |

TABLE P-continued

Effect of DTAB on various luciferases' activity

| | Average RLU over time (min) | | | |
|---|---|---|---|---|
| Enzyme/time (min) | pH 6.0 | pH 6.0 + DTAB | pH 8.0 | pH 8.0 + DTAB |
| | LucPpe2m146 | | | |
| 0 | 7685.01 | 5945.34 | 6652.84 | 6445.57 |
| 61 | 7077.29 | 5989.65 | 6577.91 | 6214.56 |
| 125 | 5507.01 | 3754.71 | 5192.73 | 4018.92 |
| 183 | 6144.94 | 4839.58 | 5476.86 | 4020.56 |
| 237 | 6471.76 | 4951.0 | 5174.22 | 3734.59 |
| Half life (min) | 820.8 | 682.6 | 595.5 | 268.0 |

*time 0 is about 2-3 minutes after mixing of enzyme and substrate

Example 7

Enhanced Duration of Luminescence and Effects of Various Media and Sera on ATP Measurement In some embodiments, the compositions of the invention were added to intact cells to lyse them, and then ATP detected. In other embodiments, conditioned culture media were themselves assayed for ATP. However, the various components of media, such as buffers, sugars, amino acids, pH indicators, salts, etc., as well as the various factors found in serum (equine, bovine, etc.) may inhibit luciferase activity. This example demonstrates the effect of cell culture media and sera in the presence of the ATPase inhibitor DTAB on the reagent composition and on the duration of luminescence (referred to herein as "signal stability") when the reagent composition is combined with a sample supplying ATP.

The following reagent composition was prepared: 40 mM Citrate buffer (pH 6.0), 110 mM MES buffer (pH 6.0), 0.2 mM EDTA, 100 µg/ml Luciferase (LucPpe2m146, diluted from 37.8 mg/ml stock solution), 5 mM luciferin, 300 mM NaCl, 20 mM MgSO$_4$, 0.05% Mazu DF-204, and varying concentrations DTAB as listed in Table Q below. The luciferase-luciferin reaction was initiated by combining 100 µl of the reagent composition with 100 µl cell media with serum, varying final concentrations of DTAB (as indicated below in Table Q) and 1.0 µM ATP was added to each reaction plus or minus 10 µM sodium pyrophosphate in wells of a 96-well microtiter luminometer plate; each experimental condition was prepared in triplicate. At various times after initiating the reaction, RLU values were recorded using an Orion microplate luminometer (Berthold Detection Systems; Pforzheim, Germany). Average RLUs and signal stability (measured in terms of its half-life) are reported in Table Q. In all media tested, the DTAB in the presence of Ppi resulted in a longer half-life than did the DTAB in the absence of the Ppi. The type of media used in the assay did not contribute significantly to signal stability variation. The signal stability half life was calculated from the time 0 (A) and from time 10 min as the original value (B). The Ppi decreased luminescence about ten-fold or more.

TABLE Q

Effects of media and sera on luciferase-luciferin reaction

| Conditions[1] | Average relative light units over time (min) | | | | | | | Signal stability $t_{1/2}$ (hr) | |
|---|---|---|---|---|---|---|---|---|---|
| | 0 | 10 | 30 | 65 | 120 | 180 | 325 | A | B |
| DMEM + 10% FBS + ATP + | | | | | | | | | |
| 0.50% DTAB | 204771 | 223493 | 187757 | 146766 | 104150 | 72609 | 32307 | 1.9 | 1.9 |
| 0.55% DTAB | 52107 | 59799 | 51285 | 42155 | 32891 | 24137 | 12031 | 2.4 | 2.3 |
| 0.45% DTAB/Ppi | 4989 | 4723 | 4053 | 3743 | 3611 | 3514 | 3188 | 9.6 | 11.4 |
| F12/DME + 10% FBS + ATP + | | | | | | | | | |
| 0.50% DTAB | 13467 | 13311 | 11348 | 9953 | 8127 | 6538 | 3793 | 3.0 | 3.0 |
| 0.55% DTAB | 6847 | 6952 | 6013 | 5581 | 4891 | 4329 | 3207 | 4.9 | 5.0 |
| 0.45% DTAB/Ppi | 1467 | 1342 | 1107 | 1047 | 1017 | 1036 | 937 | 10.6 | 14.2 |
| F12/DME + 10% HS + ATP + | | | | | | | | | |
| 0.50% DTAB | 88405 | 82645 | 70746 | 58749 | 44677 | 33353 | 17414 | 2.3 | 2.4 |
| 0.55% DTAB | 36615 | 36669 | 31348 | 27979 | 23778 | 19955 | 13539 | 3.8 | 3.8 |
| 0.45% DTAB/Ppi | 6124 | 5611 | 4981 | 4398 | 4163 | 3961 | 3553 | 7.7 | 9.0 |
| RPMI + 10% FBS + ATP | | | | | | | | | |
| 0.50% DTAB | 44179 | 43664 | 35909 | 26501 | 16951 | 10153 | 3268 | 1.4 | 1.4 |
| 0.55% DTAB | 21388 | 22863 | 19631 | 16848 | 12968 | 9661 | 5080 | 2.5 | 2.5 |
| 0.45% DTAB/Ppi | 3284 | 2879 | 2599 | 2381 | 2285 | 2243 | 2099 | 10.4 | 13.6 |

Example 8

Cell Number Correlates with Light Output

This experiment demonstrates that luminescence generated by use of the reagent composition in the method of the invention directly correlates with viable cell number. A simple correlation between known living-cell numbers and experimentally-determined luminescence was established.

Jurkat cells (ATCC, CRL-1990) were grown in 5% $CO_2$/95% air, 100% humidity at 37° C. and maintained in RPMI media (Sigma, R-8005) containing 10% FBS (Hyclone #SH30070), 1× non-essential amino acids (Hyclone SH30238) and 1 mM sodium pyruvate (Hyclone #SH30239). Cells were suspended at $5 \times 10^5$/ml in fresh complete medium, and 1:2 serial dilutions were prepared. Then, 100 µl of the cell dilutions were added to wells of a 96-well microtiter plate, resulting in 0-50,000 cells/well. Quadruplicate replicates were prepared. The plate was then incubated at 37° C., 5% $CO_2$ for 45 minutes. The plate was then equilibrated at 22° C. for 30 minutes. Then 100 µl reagent composition (40 mM Citrate buffer (pH 6.0), 110 mM MES buffer (pH 6.0), 2 mM EDTA, 450 mM $KPO_4$, 0.4% Prionex, 80 µg/ml Luciferase (LucPpe2m146, diluted from 37.8 mg/ml stock solution), 5 mM luciferin, 2% THESIT®, 20 mM NaF, 20 mM $MgSO_4$, 0.2% Mazu DF-204, 1.0% DTAB), was added to each well, the plate was gently shaken for 2 minutes, and incubated for 10 minutes on a Dynex MLX plate luminometer. The light output was then read in 0.5 second summed interrogations. The resulting average RLUs are reported herein below in Table R.

TABLE R

Correlation of luminescence with cell number

| Cells/well | Luminescence (RLU) | standard deviation |
|---|---|---|
| 0 | 0.07 | 0.015 |
| 49 | 1.96 | 0.233 |
| 98 | 3.27 | 0.460 |
| 195 | 6.71 | 0.307 |
| 390 | 12.34 | 0.356 |
| 781 | 23.53 | 0.367 |
| 1562 | 47.12 | 1.583 |
| 3125 | 91.77 | 1.156 |
| 6250 | 171.93 | 0.812 |
| 12500 | 346.26 | 10.739 |
| 25000 | 672.79 | 7.322 |
| 50000 | 1279.75 | 14.683 |

Example 9

Lymphoid Cells Tested with NaF

In some cells, such as lymphoid cells (e.g., Jurkat), an increase in luminescence over time in the presence of the reagent composition solution is observed. While the underlying mechanism of this increase in luminescence is not known, it is postulated that it results from the functioning of ATP-generating enzymes in this cell-type. The activity of such enzymes, if left unchecked, will result in an overestimation of ATP in a sample at the time of the assay. This experiment was designed to test the effects of sodium fluoride on luminescence when using lymphoid cells. The experiment also demonstrates the enhanced duration of luminescence produced by the LucPpe2m146 in the composition and methods of the invention.

Jurkat cells (ATCC, CRL-1990) were grown in 5% $CO_2$/95% air, 100% humidity at 37° C. and maintained in RPMI media (Sigma, R-8005) containing 10% FBS (Hyclone #SH30070), 1× non-essential amino acids (Hyclone SH30238) and 1 mM sodium pyruvate (Hyclone #SH130239). Cells were plated at 0, 12500, 25000, and 50000 cells/well in 100 µl of media in a 96-well microtiter luminometer plate. Quadruplicate replicates were prepared. To each of these wells was added reagent composition (reagent composition=40 mM Citrate buffer (pH 6.0), 110 mM MES buffer (pH 6.0), 0.2 mM EDTA, 0.2% Gelatin, 100 µg/ml Luciferase (LucPpe2m146, diluted from 37.8 mg/ml stock solution), 100 µM luciferin, 300 mM NaCl, 20 mM $MgSO_4$, 0.05% Mazu DF-204, 0.6% DTAB). In addition, all but the "no $KPO_4$" control sample contained 60 mM $KPO_4$ buffer (pH 6.0). Various concentrations of NaF were then added to the above solution to final concentrations of 0, 1.0, 2.0, 4.0, 10.0 mM; one condition had 10.0 mM NaF but without $KPO_4$.

Total reaction volume per well was 200 µl, consisting of 100 µl cells plus media and 100 µl reagent composition containing $KPO_4$ and/or NaF. The light output was taken at various times on a Dynex microtiter plate luminometer at a 0.5 second read time. The resulting average RLUs from quadruplicate wells and calculated signal stabilities as measured by their half-life values are reported in Table S.

The data demonstrate that the addition of NaF can inhibit the luminescence increase seen when using Jurkat cells in a method of the present invention.

TABLE S

Effect of NaF on Jurkat cell luminescence

| Cells/Well | Average RLU over time (min) | | | | | | | $t_{1/2}$ (hrs) |
|---|---|---|---|---|---|---|---|---|
| | 0 | 30 | 85 | 130 | 220 | 255 | 285 | |
| Control | | | | | | | | |
| 0 | 2.84 | 2.77 | 3.28 | 4.30 | 3.98 | 4.00 | 3.97 | — |
| 12500 | 355.70 | 370.90 | 420.87 | 470.88 | 508.06 | 523.80 | 536.11 | nc* |
| 25000 | 761.86 | 857.57 | 1174.30 | 1599.85 | 2709.75 | 3099.69 | 3276.71 | nc |
| 50000 | 1409.87 | 1946.82 | 5067.54 | 12596.83 | 4991.96 | 3583.77 | 2978.22 | nc |
| 1.0 mM NaF (in the reagent composition) | | | | | | | | |
| 0 | 2.87 | 2.72 | 2.76 | 2.91 | 2.42 | 2.37 | 2.27 | — |
| 12500 | 358.61 | 341.31 | 331.08 | 323.54 | 271.89 | 257.06 | 247.61 | 8.8 |
| 25000 | 691.68 | 640.53 | 611.45 | 596.87 | 495.89 | 463.32 | 446.32 | 7.6 |
| 50000 | 1380.16 | 1268.49 | 1185.73 | 1147.33 | 936.82 | 862.31 | 832.15 | 6.6 |
| 2.0 mM NaF | | | | | | | | |
| 0 | 2.80 | 2.59 | 2.58 | 2.57 | 2.07 | 2.06 | 1.95 | — |
| 12500 | 348.16 | 333.48 | 323.75 | 317.48 | 258.43 | 251.90 | 239.40 | 8.6 |
| 25000 | 679.02 | 631.69 | 603.07 | 589.08 | 472.37 | 455.25 | 433.54 | 7.3 |
| 50000 | 1340.22 | 1239.83 | 1156.03 | 1111.04 | 873.26 | 829.87 | 781.80 | 6.1 |
| 4.0 mM NaF | | | | | | | | |
| 0 | 6.55 | 7.65 | 15.30 | 33.49 | 15.12 | 11.87 | 10.43 | — |
| 12500 | 367.69 | 346.05 | 335.27 | 331.07 | 275.13 | 259.58 | 251.79 | 8.6 |
| 25000 | 691.41 | 634.08 | 604.37 | 587.41 | 476.36 | 453.66 | 436.38 | 7.2 |
| 50000 | 1378.13 | 1277.41 | 1195.56 | 1139.99 | 883.49 | 853.43 | 813.31 | 6.1 |
| 10.0 mM NaF | | | | | | | | |
| 0 | 6.55 | 6.20 | 6.47 | 7.87 | 5.52 | 5.27 | 5.13 | — |
| 12500 | 364.79 | 343.44 | 331.48 | 326.32 | 271.64 | 256.88 | 248.30 | 8.5 |
| 25000 | 753.29 | 677.94 | 635.67 | 617.77 | 496.08 | 471.66 | 450.76 | 6.6 |
| 50000 | 1442.08 | 1324.67 | 1235.80 | 1181.84 | 903.44 | 870.95 | 826.48 | 5.8 |
| 10.0 mM NaF, without $KPO_4$ | | | | | | | | |
| 0 | 5.95 | 5.65 | 5.43 | 5.34 | 4.19 | 4.16 | 3.91 | — |
| 12500 | 409.57 | 400.10 | 384.84 | 371.42 | 294.12 | 283.01 | 267.78 | 7.3 |
| 25000 | 806.87 | 785.16 | 734.44 | 692.57 | 516.69 | 498.99 | 468.90 | 5.7 |
| 50000 | 1514.80 | 1449.30 | 1340.91 | 1258.88 | 889.88 | 865.24 | 807.41 | 4.9 |

*nc—not calculable due to increase in RLU values over time

REFERENCES

Aiginger, P., R. Kuzmits, H. Lang, and M. M. Muller. 1980. Changes in the ATP content of leukaemic cells induced by cytotoxic substances. *J. Clin. Chem. Clin. Biochem.* 1:216.

Andreotti, P. E., I. A. Cree, C. M. Kurbacher, D. M. Hartmann, D. Linder, G. Harel, I. Gleiberman, P. A. Caruso, S. H. Ricks, M. Untch, and et al. 1995. Chemosensitivity testing of human tumors using a microplate adenosine triphosphate luminescence assay: clinical correlation for cisplatin resistance of ovarian carcinoma. *Cancer Res.* 55:5276-82.

Ausubel, F. M., R. Brent, R. E. Kingston, D. D. Moore, J. G. Seidman, J. A. Smith, and K. Struhl. 1987. Current protocols in molecular biology. John Wiley & Sons, New York.

Baldwin, T. O., and V. A. Green. 2000. Purification of firefly luciferase from recombinant sources. *Methods Enzymol.* 305:180-8.

Beny, M., and M. Dolivo. 1976. Separation of firefly luciferase using an anion exchanger. *FEBS Lett.* 70:167-70.

Bostick, W. D., M. S. Denton, and S. R. Dinsmore. 1982. Liquid-chromatographic separation and bioluminescent detection of creatine kinase iso enzymes. In Bioluminescence and Chemiluminescence: Instruments and Applications. Vol. II. K. Van Dyke, editor. CRC Press, Boca Raton, Fla. 227-246.

Bowie, L. J., V. Horak, and M. De Luca. 1973. Synthesis of a new substrate analog of firefly luciferin. An active-site probe. *Biochemistry.* 12:1845-52.

Bradbury, D. A., T. D. Simmons, K. J. Slater, and S. P. Crouch. 2000. Measurement of the ADP:ATP ratio in human leukaemic cell lines can be used as an indicator of cell viability, necrosis and apoptosis. *J Immunol Methods.* 240:79-92.

Branchini, B. R. 2000. Chemical synthesis of firefly luciferin analogs and inhibitors. *Methods Enzymol.* 305:188-95.

Branchini, B. R., M. M. Hayward, S. Bamford, P. M. Brennan, and E. J. Lajiness. 1989. Naphthyl- and quinolylluciferin: green and red light emitting firefly luciferin analogues. *Photochem Photobiol.* 49:689-95.

Branchini, B. R., T. M. Marschner, and A. M. Montemurro. 1980. A convenient affinity chromatography-based purification of firefly luciferase. *Anal Biochem.* 104:386-96.

Carter, P. 1986. Site-directed mutagenesis. *Biochem J.* 237:1-7.

Craig, F. F., A. C. Simmonds, D. Watmore, F. McCapra, and M. R. White. 1991. Membrane-permeable luciferin esters for assay of firefly luciferase in live intact cells. *Biochem J.* 276:637-41.

Cree, I. A. 1998. Luminescence-based cell viability testing. *Methods Mol Biol.* 102:169-77.

Cree, I. A., and P. E. Andreotti. 1997. Measurement of Cytotoxicity by ATP-based Luminescence Assay in Primary Cell Cultures and Cell Lines. *Toxicology in Vitro.* 11:553-556.

Crouch, S. P., R. Kozlowski, K. J. Slater, and J. Fletcher. 1993. The use of ATP bioluminescence as a measure of cell proliferation and cytotoxicity. *J Immunol Methods.* 160:81-8.

Demerec, M., E. A. Adelberg, A. J. Clark, and P. E. Hartman. 1966. A proposal for a uniform nomenclature in bacterial genetics. *Genetics.* 54:61-76.

Ebadi, M. S. 1972. Firefly luminescence in the assay of cyclic AMP. *Adv Cyclic Nucleotide Res.* 2:89-109.

Filippova, N. Y., A. F. Dukhovich, and N. N. Ugarova. 1989. New approaches to the preparation and application of firefly luciferase. *J Biolumin Chemilumin.* 4:419-22.

Hastings, J. W. 1996. Chemistries and colors of bioluminescent reactions: a review. *Gene.* 173:5-11.

Hastings, J. W., and T. Wilson. 1976. Bioluminescence and chemiluminescence. *Photochem Photobiol.* 23:461-73.

Jassim, S. A., A. Ellison, S. P. Denyer, and G. S. Stewart. 1990. In vivo bioluminescence: a cellular reporter for research and industry. *J Biolumin Chemilumin.* 5:115-22.

Jones, K., F. Hibbert, and M. Keenan. 1999. Glowing jellyfish, luminescence and a molecule called coelenterazine. *Trends Biotechnol.* 17:477-81.

Kajiyama, N., and E. Nakano. 1993. Thermostabilization of firefly luciferase by a single amino acid substitution at position 217. *Biochemistry.* 32:13795-9.

Kajiyama, N., and E. Nakano. 1994. Enhancement of thermostability of firefly luciferase from *Luciola lateralis* by a single amino acid substitution. *Biosci Biotechnol Biochem.* 58:1170-1.

Kangas, L., M. Gronroos, and A. L. Nieminen. 1984. Bioluminescence of cellular ATP: a new method for evaluating cytotoxic agents in vitro. *Med Biol.* 62:338-43.

Kiechle, F. L., L. Jarett, D. A. Popp, and N. Kotagal. 1980. Isolation from rat adipocytes of a chemical mediator for insulin activation of pyruvate dehydrogenase. *Diabetes.* 29:852-5.

Kricka, L. J., and M. De Luca. 1982. Effect of solvents on the catalytic activity of firefly luciferase. *Arch Biochem Biophys.* 217:674-81.

Lundin, A., J. Anson, and P. Kau. 1994. ATP extractants neutralised by cyclodextrins. In Bioluminescence and Chemiluminescence: Fundamental and Applied Aspects. A. K. Campbell, L. J. Kricka, and P. E. Stanley, editors. John Wily & Sons, New York. 399-402.

McElroy, W. D., H. H. Seliger, and E. H. White. 1969. Mechanism of bioluminescence, chemiluminescence and enzyme function in the oxidation of firefly luciferin. *Photochem Photobiol.* 10:153-70.

Miska, W., and R. Geiger. 1987. Synthesis and characterization of luciferin derivatives for use in bioluminescence enhanced enzyme immunoassays. New ultrasensitive detection systems for enzyme immuno assays, I. *J Clin Chem Clin Biochem.* 25:23-30.

Missiaen, L., F. Wuytack, H. De Smedt, M. Vrolix, and R. Casteels. 1988. A1F4-reversibly inhibits 'P'-type cation-transport ATPases, possibly by interacting with the phosphate-binding site of the ATPase. *Biochem J.* 253:827-33.

Morii, M., and N. Takeguchi. 1993. Different biochemical modes of action of two irreversible H+,K(+)-ATPase inhibitors, omeprazole and E3810. *J Biol Chem.* 268:21553-9.

Moyer, J. D., and J. F. Henderson. 1983. Nucleoside triphosphate specificity of firefly luciferase. *Anal Biochem.* 131:187-9.

Nguyen, V. T., M. Morange, and O. Bensaude. 1988. Firefly luciferase luminescence assays using scintillation counters for quantitation in transfected mammalian cells. *Anal Biochem.* 171:404-8.

Petty, R. D., L. A. Sutherland, E. M. Hunter, and I. A. Cree. 1995. Comparison of MTT and ATP-based assays for the measurement of viable cell number. *J Biolumin Chemilumin.* 10:29-34.

Picciolo, G. L., E. W. Chappelle, R. R. Thomas, and M. A. McGarry. 1977. Performance characteristics of a new photometer with a moving filter tape for luminescence assay. *Appl Environ Microbiol.* 34:720-4.

Ronner, P., E. Friel, K. Czerniawski, and S. Frankle. 1999. Luminometric assays of ATP, phosphocreatine, and creatine for estimation of free ADP and free AMP. *Anal Biochem.* 275:208-16.

Sambrook, J. 1989. Molecular cloning: a laboratory manual. Cold Spring Harbor Laboratory, Cold Spring Harbor.

U.S. Pat. No. 5,618,682.1997. BIOLUMINESCENCE MEASUREMENT SYSTEM. US.

U.S. Pat. No. 5,866,348.1999. BIOLUMINESCENCE MEASUREMENT SYSTEM. US.

Simpson, W. J., and J. R. Hammond. 1991. The effect of detergents on firefly luciferase reactions [published erratum appears in J Biolumin Chemilumin 1991 July-September; 6 (3):146]. *J Biolumin Chemilumin.* 6:97-106.

Stanley, P. E. 1989. A review of bioluminescent ATP techniques in rapid microbiology. *J Biolumin Chemilumin.* 4:375-80.

Thomson, C. M., P. J. Herring, and A. K. Campbell. 1997. The widespread occurrence and tissue distribution of the imidazolopyrazine luciferins. *J Biolumin Chemilumin.* 12:87-91.

WO 00/18953. 2000. Method for detecting ATP. PCT.

Vaskinn, S., E. Sundkvist, R. Jaeger, and G. Sager. 1999. The effect of Mg2+, nucleotides and ATPase inhibitors on the uptake of [3H]-cGMP to inside-out vesicles from human erythrocytes. *Mol Membr Biol.* 16:181-8.

Wells, J. A., M. Vasser, and D. B. Powers. 1985. Cassette mutagenesis: an efficient method for generation of multiple mutations at defined sites. *Gene.* 34:315-23.

White, E. H., E. Rapaport, T. A. Hopkins, and H. H. Seliger. 1969. Chemi- and bioluminescence of firefly luciferin. *J Am Chem Soc.* 91:2178-80.

White, H. E., J. D. Miano, and M. Umbreit. 1975. Letter: on the mechanism of firefly luciferin luminescence. *J Am Chem Soc.* 97:198-200.

White, P. J., D. J. Squirrell, P. Arnaud, C. R. Lowe, and J. A. Murray. 1996. Improved thermostability of the North American firefly luciferase: saturation mutagenesis at position 354. *Biochem J.* 319:343-50.

Wilson, T., and J. W. Hastings. 1998. Bioluminescence. *Annu Rev Cell Dev Biol.* 14:197-230.

U.S. Pat. No. 5,283,179.1994. LUCIFERASE ASSAY METHOD. US.

U.S. Pat. No. 5,650,289.1997. LUCIFERASE ASSAY COMPOSITIONS. US.

WO 9914336. 1999. Thermostable luciferases and methods of production. PCT.

Wood, K. V., Y. A. Lam, and W. D. McElroy. 1989. Introduction to beetle luciferases and their applications. *J Biolumin Chemilumin.* 4:289-301.

Yang, J., and D. B. Thomason. 1993. An easily synthesized, photolyzable luciferase substrate for in vivo luciferase activity measurement. *Biotechniques.* 15:848-50.

Ye, L., L. M. Buck, H. J. Schaeffer, and F. R. Leach. 1997. Cloning and sequencing of a cDNA for firefly luciferase from *photuris pennsylvanica*. *Biochim Biophys Acta.* 1339:39-52.

Zoller, M. J., and M. Smith. 1987. Oligonucleotide-directed mutagenesis: a simple method using two oligonucleotide primers and a single-stranded DNA template. *Methods Enzymol.* 154:329-50.

---

We claim:

1. A kit for detecting ATP comprising:
   a luciferase component comprising a chemostable variant of a beetle luciferase having at least 95% amino acid sequence identity to any of SEQ ID NOS: 1, 2, 3, or 4; and
   an ATPase inhibitor component comprising one or more ATPase inhibitors,
   the chemostable variant retaining greater luminescence activity measured by luminescence after contact with the ATPase inhibitor for at least one hour compared to the wild type beetle luciferase.

2. The kit of claim 1, where the combination of the luciferase component and the ATPase inhibitor component forms a reagent composition for detecting ATP in a sample; where the reagent composition maintains at least about 30% activity, as measured by luminescence after the reagent composition is combined with the sample, for at least one hour after the reagent composition is combined with a sample containing ATP, as compared to the reagent composition's activity just after the luciferase is combined with the one or more ATPase inhibitors, and where the one or more ATPase inhibitors present in the reagent composition are collectively able to reduce ATPase activity endogenous to the sample by at least about 25% relative to the sample's ATPase activity in the absence of the one or more ATPase inhibitors.

3. The kit of claim 1, where the luciferase component comprises a lyophilized preparation of a chemostable luciferase.

4. The kit of claim 1, where the kit further comprises a luciferin.

5. The kit of claim 1, where the ATPase inhibitor comprises a detergent.

6. The kit of claim 5, where the detergent is selected from the group consisting of: a cationic detergent, an anionic detergent and a zwitterionic detergent.

7. The kit of claim 1, where the kit further comprises an enzyme stabilizing agent.

8. The kit of claim 1, where the chemostable variant of the beetle luciferase comprises the peptide sequence of SEQ ID NO:4 with one or more conservative amino acid substitutions selected from the group consisting of: a substitution of Glu for Asp, substitution of Ala for Gly, substitution of Leu for Ile, substitution of Arg for Lys, substitution of Tyr for Phe, substitution of Thr for Ser.

9. A kit for detecting ATP in a sample, the kit comprising:
   a luciferase component comprising a chemostable luciferase, the chemostable luciferase selected from a panel of luciferase variants having at least 95% amino acid sequence identity to a wild-type luciferase; and
   an ATPase inhibitor component comprising one or more ATPase inhibitors selected from one or more detergents, where combination of the luciferase component and the ATPase component forms a reagent composition comprising the chemostable luciferase and the one or more detergents, with the chemostable luciferase having a rate of decline in enzymatic activity after contact with the ATPase inhibitor in the reagent composition measured by a luminescence characterized by a first half life that is greater than a second half life measured for the wild-type luciferase in the ATPase inhibitor.

10. The kit of claim 9, where the chemostable luciferase maintains at least 30% luminescence activity one hour after the reagent composition is combined with a sample comprising ATP, as compared to the reagent composition's activity immediately after the combining the reagent composition with the sample, and where the one or more detergents present in the reagent composition are collectively able to reduce ATPase activity endogenous to the sample by at least 25% relative to the sample's ATPase activity in the absence of the one or more ATPase inhibitors.

11. The kit of claim 10, where the chemostable luciferase is a chemostable variant of a luciferase of SEQ ID NO:4 retaining greater luminescence activity measured by luminescence after contact with an ATPase inhibitor for at least one hour compared to the luciferase of SEQ ID NO:4.

12. A kit for detecting ATP, the kit comprising:
   a luciferase component comprising a chemostable variant having at least 90% amino acid sequence identity to *P. pennsylvanica* beetle luciferase (LucPe2); and
   an ATPase inhibitor component comprising one or more ATPase inhibitors selected from one or more detergents; the chemostable variant retaining greater enzymatic activity after contact with the ATPase inhibitor compared to the wild type beetle luciferase, the enzymatic activity after contact with the ATPase inhibitor measured by luminescence characterized by a first half life that is greater than a second half life measured for the wild-type bettle luciferase in the ATPase inhibitor.

13. The kit of claim 12, where the chemostable variant has a rate of decline in enzymatic activity after contact with the ATPase inhibitor measured by luminescence characterized by a first half life that is greater than a second half life measured for the luciferase of SEQ ID NO:4 in the ATPase inhibitor.

14. The kit of claim 13, where the kit is further characterized in that:
   a. the chemostable variant of the beetle luciferase is a variant luciferase of SEQ ID NO:4 with an amino acid substitution, retaining greater luminescence activity measured by luminescence after contact with an ATPase inhibitor for at least one hour compared to the luciferase of SEQ ID NO:4;
   b. the chemostable variant has a rate of decline in enzymatic activity after contact with the ATPase inhibitor measured by luminescence characterized by a first half life that is greater than a second half life measured for the luciferase of SEQ ID NO:4 in the ATPase inhibitor;
   c. the chemostable variant of the beetle luciferase comprises the peptide sequence of SEQ ID NO:4 with one or more conservative amino acid substitutions selected from the group consisting of: a substitution of Glu for Asp, substitution of Ala for Gly, substitution of Leu for Ile, substitution of Arg for Lys, substitution of Tyr for Phe, substitution of Thr for Ser;
   d. the luciferase component further comprises a luciferin;
   e. the ATPase inhibitor comprises a detergent selected from the group consisting of: a cationic detergent, an anionic detergent and a zwitterionic detergent; and
   f. the luciferase component comprises a lyophilized preparation of a chemostable luciferase.

* * * * *